US011007169B2

(12) United States Patent
Gao et al.

(10) Patent No.: US 11,007,169 B2
(45) Date of Patent: May 18, 2021

(54) CIS-GNETIN H AND TRANS-GNETIN H AS THERAPEUTIC AGENTS

(71) Applicant: MIDDLE TENNESSEE STATE UNIVERSITY, Murfreesboro, TN (US)

(72) Inventors: Ying Gao, Murfreesboro, TN (US); Elliot Altman, Rockvale, TN (US); Anthony Farone, Murfreesboro, TN (US); Hyo Park, Shelbyville, TN (US)

(73) Assignee: Middle Tennessee State University, Murfreesboro, TN (US)

( * ) Notice: Subject to any disclaimer, the term of this patent is extended or adjusted under 35 U.S.C. 154(b) by 0 days.

(21) Appl. No.: 16/265,789

(22) Filed: Feb. 1, 2019

(65) Prior Publication Data
US 2019/0290611 A1  Sep. 26, 2019

Related U.S. Application Data

(63) Continuation of application No. 15/513,375, filed as application No. PCT/US2015/051424 on Sep. 22, 2015, now abandoned.

(60) Provisional application No. 62/053,497, filed on Sep. 22, 2014.

(51) Int. Cl.
| A61K 31/343 | (2006.01) |
| A61K 45/06 | (2006.01) |
| A61K 36/65 | (2006.01) |
| A61K 39/00 | (2006.01) |

(52) U.S. Cl.
CPC ............ *A61K 31/343* (2013.01); *A61K 36/65* (2013.01); *A61K 39/00* (2013.01); *A61K 45/06* (2013.01); *A61K 2236/17* (2013.01); *A61K 2236/333* (2013.01)

(58) Field of Classification Search
CPC .................................................. A61K 31/343
See application file for complete search history.

(56) References Cited

U.S. PATENT DOCUMENTS

| 2003/0073712 A1* | 4/2003 | Wang ...................... A61P 17/02 514/277 |
| 2004/0266713 A1 | 12/2004 | Lu et al. |
| 2008/0262081 A1 | 10/2008 | Raederstorff et al. |
| 2013/0184342 A1* | 7/2013 | Mills .......................... A61P 1/16 514/516 |
| 2014/0199296 A1 | 7/2014 | Bannister et al. |
| 2017/0326098 A1 | 11/2017 | Gao et al. |

FOREIGN PATENT DOCUMENTS

| CN | 1729007 A | 2/2006 |
| CN | 103272007 A | 9/2013 |
| WO | WO 03/039557 A1 | 5/2003 |
| WO | WO 2006/126751 A1 | 11/2006 |
| WO | WO 2013/003112 A1 | 1/2013 |

OTHER PUBLICATIONS

Cai et al., Suppression of the onset and progression of collagen-induced arthritis in rats by QFGJS, a preparation from an anti-arthritic Chinese herbal formula, Journal of Ethnopharmacology 110 (2007) 39-48.*
He et al., Simultaneous determination of ten stilbenes in the seeds of *Paeonia* species using HPLC-DAD, J. Liquid Chromatography & Related Technologies, 36:1708-1724, 2013.*
Kim et al., Cytototoxic and Antimutagenic Stilbenes from Seeds of Paeonia lactiflora, Arch Pharm Res, vol. 25 (3), 293-299, 2002.*
Abraham et al., "Antiinflammatory effects of dexamethasone are partly dependent on induction of dual specificity phosphatase 1," *J. Exp. Med.*, Aug. 7, 2006; 203(8):1883-9.
Aggarwal, "Signalling pathways of the TNF superfamily: a double-edged sword," *Nature Rev. Immunol.*, Sep. 2003; 3(9):745-756.
Aggarwal et al., "Role of Resveratrol in Prevention and Therapy of Cancer: Preclinical and Clinical Studies," *Anticancer Res.*, 2004; 24:2783-2840.
An et al., "Epidermal growth factor receptor inhibition sensitizes renal cell carcinoma cells to the cytotoxic effects of bortezomib," *Mol. Cancer Ther.*, Jan. 2007; 6(1):61-9.
Anisimova et al., "Trans-, cis-, and dihydro-resveratrol: a comparative study," *Chem. Cent. J.*, 2011; 5(88):1-6 ; doi:10.1186/1752-153X-5-88.
Athearn et al., "Acute Reactogenicity after Intramuscular Immunization with Recombinant Vesicular Stomatitis Virus Is Linked to Production of IL-1β," *PLoS One*, Epub Oct. 8, 2012; 7(10):e46516, doi: 10.1371/journal.pone.0046516.
Badger et al., "Idoxifene, a Novel Selective Estrogen Receptor Modulator, Is Effective in a Rat Model of Adjuvant-Induced Arthritis," *The Journal of Pharmacology and Experimental Therapeutics*, 1999; 291(3):1380-1386.
Bai et al., "Resveratrol induces apoptosis and cell cycle arrest of human T24 bladder cancer cells in vitro and inhibits tumor growth in vivo." *Cancer Sci.*, Feb. 2010; 101(2):488-493.
Benitez et al., "Mechanisms Involved in Resveratrol-Induced Apoptosis and Cell Cycle Arrest in Prostate Cancer-Derived Cell Lines," *J. Androlog.*, Mar./Apr. 2007; 28(2):282-293.
Bezalel et al., "Novel biological treatments for systemic lupus erythematosus: current and future modalities," *Isr. Med. Assoc. J.*, Aug. 2012; 14(8):508-14.
Bingham, "The stereochemical consequences of electron delocalization in extended .pi. systems. An interpretation of the cis effect exhibited by 1,2-disubstituted ethylenes and related phenomena," *J. Am. Chem. Soc.*, Jan. 1976; 98(2):535-540.
Bishayee, "Cancer Prevention and Treatment with Resveratrol: From Rodent Studies to Clinical Trials," *Cancer Prev. Res.*, May 2009; 2(5):409-418.

(Continued)

*Primary Examiner* — Svetlana M Ivanova
(74) *Attorney, Agent, or Firm* — Mueting Raasch Group

(57) ABSTRACT

The cis-isomer and trans-isomers of the plant-derived compound gnetin H are shown have anticancer properties, anti-inflammatory properties, and low toxicity. Therapeutic and prophylactic compositions that contain cis-gnetin H, trans-gnetin H, and derivatives thereof, as well as methods of making and using said compositions, are provided. cis-gnetin H and/or trans-gnetin H can be used in purified form or as a plant extract.

10 Claims, 26 Drawing Sheets

(56) References Cited

OTHER PUBLICATIONS

Bjarnason et al., "Side effects of nonsteroidal anti-inflammatory drugs on the small and large intestine in humans," *Gastroenterology*, Jun. 1993; 104(6):1832-47.
Bonda et al., "The Photostability and Photostabilization of trans-Resveratrol," *Cosmetics & Toiletries magazine*, Sep. 2011; 126(9):652-660.
Bongartz et al., "Anti-TNF Antibody Therapy in Rheumatoid Arthritis and the Risks of Serious Infections and Malignancies: Systematic Review and Meta-analysis of Rare Harmful Effects in Randomized Controlled Trials," *JAMA*, May 2006; 295(19): 2275-2285.
Buss et al., "Cyclin-Dependent Kinase 6 Phosphorylates NF-κB P65 at Serine 536 and Contributes to the Regulation of Inflammatory Gene Expression," *PLoS One*, Dec. 2012; 7(12):e51847, 1-13.
Cai et al., "Suppression of the onset and progression of collagen-induced arthritis in rats by QFGJS, a preparation from an antiarthritic Chinese herbal formula" J Ethnopharmacol, 110 (2007) 39-48.
Chanput et al., "THP-1 cell line: an in vitro cell model for immune modulation approach," *Int. Immunopharmacol.*, Nov. 2014; Epub Aug. 14, 2014; 23(1):37-45.
Choi et al., "In Vitro BACE-1 Inhibitory Activity of Resveratrol Oligomers from the Seed Extract of *Paeonia lactiflora*," *Planta Med.*, 2011; 77:374-376.
Choi et al., "Ethanol extract of paeonia suffruticosa Andrews (PSE) induced AGS human gastric cancer cell apoptosis via fas-dependent apoptosis and MDM2-p53 pathways," *J. Biomed. Sci.*, 2012, 19:82, doi:10.1186/1423-0127-19-82 (12 pp).
Cyr et al., "Cell Cycle Arrest and Apoptosis Responses of Human Breast Epithelial Cells to the Synthetic Organosulfur Compound p-methoxyphenyl p-Toluenesulfonate," *Anticancer Res.*, 2008; 28:2753-2764.
Diamantopoulos et al., "Is it safe to use TNF-α blockers for systemic inflammatory disease in patients with heart failure? Importance of dosage and receptor specificity," *Int. J. Cardiol.*, Sep. 2013; Epub Dec. 14, 2012; 167(5):1719-1723.
Dörrie et al., "Resveratrol induces extensive apoptosis by depolarizing mitochondrial membranes and activating caspase-9 in acute lymphoblastic leukemia cells," *Cancer Res.*, Jun. 2001; 61(12):4731-4739.
Escárcega et al., "The Transcription Factor Nuclear Factor-kappa B and Cancer," *Clin. Oncol.*, Mar. 2007; 19(2):154-161.
Fischer et al., "The thermodynamic equilibrium between cis- and trans-isomers in stilbene and some derivatives," *J. Chem. Soc. B.*, Jan. 1968; 0:1156-1158.
Ganchi et al., "I kappa B/MAD-3 masks the nuclear localization signal of NF-kappa B p65 and requires the transactivation domain to inhibit NF-kappa B p65 DNA binding," *Mol. Biol. Cell.*, Dec. 1992; 3(12):1339-1352.
Gao et al., "The resveratrol oligomers, cis- and trans-gnetin H, from *Paeonia suffruticosa* seeds inhibit the growth of several human cancer cell lines," *J. Ethnopharmacol.*, Epub Apr. 9, 2015; 169:24-33.
Ha et al., "Stilbenes and oligostilbenes from leaf and stem of Vitis amurensis and their cytotoxic activity," *Arch. Pharm. Res.*, Feb. 2009; 32(2):177-83.
Harper et al., "The p21 Cdk-interacting protein Cip1 is a potent inhibitor of G1 cyclin-dependent kinases," *Cell*, Nov. 1993; 75(4):805-816.
He et al., "Three New Oligostilbenes from the Seeds of *Paeonia suffruticosa*," *Chem. Pharm. Bull.*, Jun. 2010; 58(6):843-847.
He et al., "Simultaneous Determination of Ten Stilbenes in the Seeds of *Paeonia* Species Using HPLC-DAD," *J. Liq. Chromatog. Rel. Technol.*, Epub Dec. 20, 2012; 36(12):1708-1724.
Horvath et al., "Novel resveratrol derivatives induce apoptosis and cause cell cycle arrest in prostate cancer cell lines," *Anticancer Res.*, 2007; 27(5A):3459-3464.
Hu et al., "Paeonol, the main active principles of Paeonia moutan, ameliorates alcoholic steatohepatitis in mice," *J. Ethnopharmacol.*, Mar. 2010, 128(1):100-6.

Hwang et al., "Reduction of anion exchanger 2 expression induces apoptosis of human hepatocellular carcinoma cells," *Mol. Cell Biochem.*, 2009; 327:134-144.
Impellizzeri et al., "Targeting inflammation: new therapeutic approaches in chronic kidney disease (CKD)," *Pharmacol. Res.*, Mar. 3, 2014, 81:91-102.
Israël, "The IKK complex, a central regulator of NF-kappaB activation," *Cold Spring Harb. Perspect. Biol.*, Mar. 2010; 2(3):a000158, 1-14.
Juliana et al., "Anti-inflammatory compounds parthenolide and Bay 11-7082 are direct inhibitors of the inflammasome," *J. Biol. Chem.*, Mar. 2010; 285(13):9792-802.
Kang et al., "Resveratrol derivatives potently induce apoptosis in human promyelocytic leukemia cells. Experimental and molecular medicine," *Exp. Mol. Med.*, Dec. 2003; 35(6):467-474.
Kim et al., "Antioxidative Activity of Resveratrol and Its Derivates Isolated from Seeds of Paeonia lactiflora," *Biosci. Biotechnol. Biochem.*, 2002; 66(9):1990-1993.
Kim Hyo-Jin et al., "Cytotoxic and Antimutagenic Stilbenes from Seeds of Paeonia lactiflora," Archives of Pharmacal Research, Natl., Fisheries University, Pusan, KR, Jun. 1, 2002; 25(3):293-299; English Abstract Only.
Kim et al., "Cytotoxic and Antimutagenic Stilbenes from Seeds of Paeonia lactiflora," *Arch. Pharm. Res.*, 2002; 25(3):293-299.
Kohn et al., "Molecular interaction map of the mammalian cell cycle control and DNA repair systems," *Mol. Biol. Cell.*, Aug. 1999; 10:2703-2734.
Konno et al., "Melinjo (Gnetum gnemon L.) Seed Extract Decreases Serum Uris Acid Levels in Nonobese Japanese Males: A Randomized Controlled Study," *Evidence-Based Complementary and Alternative Medicine*, Epub Dec. 17, 2013; 2013:Article ID 589169 (9 pp).
Laird et al., "TLR4/MyD88/PI3K interactions regulate TLR4 signaling," *J. Leukoc. Biol.*, Jun. 2009; 85(6):966-77.
Lao et al., "Autophagy Pathway of Raji Cell Death Induced by Resveratrol," *Chin. J. Biologicals*, Jul. 2009; 22(7):654-8.
Lee et al., "MEKK1 activates both IkappaB kinase alpha and IkappaB kinase beta," *Proc. Nat'l. Acad. Sci. USA*, Aug. 1998; 95(16):9319-9324.
Lee et al., "Potent inhibition of Lewis lung cancer growth by heyneanol A from the roots of Vitis amurensis through apoptotic and anti-angiogenic activities," *Carcinogenesis*, Oct. 2006; 27(10):2059-2069.
Lewis et al., "Application of "Systems Vaccinology" to Evaluate Inflammation and Reactogenicity of Adjuvanted Preventative Vaccines," *J Immunol Res.*, Epub Aug. 25, 2015; 2015:909406 (11 pp).
Li et al., "2,3',4,4',5'-Pentamethoxy-trans-stilbene, a resveratrol derivative, inhibits, colitis-associated colorectal carcinogenesis in mice," *British Journal of Pharmacology*, 2010; 160:1352-1361.
Lin et al., "Natural Oligostilbenes," *Stud. Nat. Prod. Chem.*, 2006; 33:601-644.
Liu et al., "Resveratrol inhibits human lung adenocarcinoma cell metastasis by suppressing heme oxygenase 1-mediated nuclear factor-κB pathway and subsequently downregulating expression of matrix metalloproteinases," *Mol. Nutr. Food Res.*, Jul. 2010; 54 Suppl 2:S196-S204.
Li-Weber, "Targeting apoptosis pathways in cancer by Chinese medicine," *Cancer Lett.* 2010; 332(2):304-312.
Manna et al., "Resveratrol suppresses TNF-induced activation of nuclear transcription factors NF-kappa B, activator protein-1, and apoptosis: potential role of reactive oxygen intermediates and lipid peroxidation," *J. Immunol.*, Jun. 2000; 164(12):6509-19.
Medvedev et al., "Dysregulation of LPS-induced Toll-like receptor 4-MyD88 complex formation and IL-1 receptor-associated kinase 1 activation in endotoxin-tolerant cells," *J. Immunol.*, Nov. 2002; 169(9):5209-16.
Mercurio et al., "IKK-1 and IKK-2: cytokine-activated IkappaB kinases essential for NF-kappaB activation," *Science*, Oct. 1997; 278(5339):860-6.
Minamikawa et al., "Mitochondrial permeability transition and swelling can occur reversibly without inducing cell death in intact human cells," *Exp. Cell Res.*, Jan. 1999; 246(1):26-37.

(56) References Cited

OTHER PUBLICATIONS

Moreno et al., "Specification of the NF-kappaB transcriptional response by p65 phosphorylation and TNF-induced nuclear translocation of IKK epsilon," *Nucl. Acids Res.*, Oct. 2010, 38(18):6029-44.
Newmeyer et al., "Mitochondria: releasing power for life and unleashing the machineries of death," *Cell*, Feb. 2003; 112(4):481-490.
Oh et al., "Inhibitory effects of the root cortex of Paeonia suffruticosa on interleukin-8 and macrophage chemoattractant protein-1 secretions in U937 cells," *J. Ethnopharmacol.*, Jan. 2003, 84(1):85-9.
"Pathogen Induced Chronic Inflammatory Disorders," Boston University School of Medicine Host Pathogen Interactions, Retrieved Oct. 19, 2017; http://www.bumc.bu.edu/gencolab/research/pathogen-induced-chronic-inflammatory-disorders/.
Pettit et al., "Antineoplastic Agents. 579. Synthesis and Cancer Cell Growth Evaluation of E-Stilstatin 3: A Resveratrol Structural Modification," *J. Nat. Prod.*, 2009; 72:1637-1642.
Pikarsky et al., "NF-κb functions as a tumour promoter in inflammation-associated cancer," *Nature*, Sep. 2004; 431(7007):461-6.
Postal et al., "The role of Tumor Necrosis Factor-alpha (TNF-α) in the pathogenesis of systemic lupus erythematosus," *Cytokine*, Dec. 2011; 56(3):537-43.
Qin et al., "TLR8-mediated NF-κB and JNK Activation Are TAK1-independent and MEKK3-dependent," *J. Biol. Chem.*, May 2006, 281(30):21013-21021.
Roman et al., "Analysis of resveratrol-induced apoptosis in human B-cell chronic leukaemia," *British Journal of Haematology*, 2002; 117:842-851.
Sakurai, "Targeting of TAK1 in inflammatory disorders and cancer," *Trends Pharmacol. Sci.*, Oct. 2012, 33(10):522-30.
Sasaki et al. "Phosphorylation of RelA/p65 on serine 536 defines an IκBα-independent NF-κB pathway," *J. Biol. Chem.*, Oct. 2005; 280(41):34538-47.
Schmitz et al., "The p65 subunit is responsible for the strong transcription activating potential of NF-kappa B, "*Embo J.*, Dec. 1991, 10(12):3805-17.
Sethi et al., "Potential pharmacological control of the NFkappaB pathway," *Trends Pharmacol. Sci.*, Jun. 2009; 30(6):313-321.
Shim et al., "TAK1, but not TAB1 or TAB2, plays an essential role in multiple signaling pathways in vivo," *Genes Dev.*, Oct. 2005, 19:2668-81.
Sizemore et al., "Distinct roles of the Ikappa B kinase alpha and beta subunits in liberating nuclear factor kappa B (NF-kappa B) from Ikappa B and in phosphorylating the p65 subunit of NF-kappa B," *J. Biol. Chem.*, Feb. 8, 2002; 277(6):3863-9. Epub Dec. 3, 2001.
Smith et al., "The role of TBK1 and IKKε in the expression and activation of Pellino 1," *Biochem. J.*, Mar. 2011, 434(3):537-48.
Steer et al., "Glucocorticoids suppress tumor necrosis factor-alpha expression by human monocytic THP-1 cells by suppressing transactivation through adjacent NF-kappa B and c-Jun-activating transcription factor-2 binding sites in the promoter," *J. Biol. Chem.*, Jun. 2000; 275(24):18432-40.
Sun et al., "Resveratrol downregulates the constitutional activation of nuclear factorkappaB in multiple myeloma cells, leading to suppression of proliferation and invasion, arrest of cell cycle, and induction of apoptosis," *Cancer Genet. Cytogenet.*, Feb. 2006; 165(1):9-19.
Tani et al., "Pharmacokinetics and Safety of Resveratrol Derivatives in Humans after Oral Administration of Melinjo (Gnetum gnemon L.) See Extract Powder," *J. Agric. Food Chem.*, Epub Feb. 12, 2014; 62(8):1999-2007.
Thalayasingam et al., "Anti-TNF therapy," *Best Pract. Res. Clin. Rheumatol.*, Aug. 2011; 25(4):549-67.
Thornberry et al., "Caspases: enemies within," *Science*, Aug. 1998; 281(5381):1312-1316.
Wang et al., "The study of resveratrol by modulating STATA3 on acute myeloblastic leukemia," *Chinese Pharmacological Bulletin*, Mar. 2010; 26(3):346-352.
Wang et al., "Naturally derived anti-inflammatory compounds from Chinese medicinal plants," *J. Ethnopharmacol.*, Mar. 2013; Epub Dec. 26, 2012; 146(1):9-39.
Warburton et al., "Treatment of HER-2/neu overexpressing breast cancer xenograft models with trastuzumab (Herceptin) and gefitinib (ZD1839): drug combination effects on tumor growth, HER-2/neu and epidermal growth factor receptor expression, and viable hypoxic cell fraction," *Clin. Cancer Res.*, Apr. 2004; 10(7):2512-2524.
Weng et al., "Mechanisms of apoptotic effects induced by resveratrol, dibenzoylmethane, and their analogues on human lung carcinoma cells," *J. Agric. Food Chem.*, Jun. 2009; 57(12):5235-5243.
Wilhelm et al., "BAY 43-9006 exhibits broad spectrum oral antitumor activity and targets the RAF/MEK/ERK pathway and receptor tyrosine kinases involved in tumor progression and angiogenesis," *Cancer Res.*, Oct. 2004; 64(19):7099-7109.
Yamamoto et al., "Role of the NF-kappaB pathway in the pathogenesis of human disease states," *Curr. Mol. Med.*, Jul. 2001; 1(3):287-96.
Yang et al., "IKK beta plays an essential role in the phosphorylation of RelA/p65 on serine 536 induced by lipopolysaccharide," *J. Immunol.*, Jun. 2003; 170(11):5630-5.
Yao et al., "Interleukin-1 (IL-1)-induced TAK1-dependent Versus MEKK3-dependent NFkappaB activation pathways bifurcate at IL-1 receptor-associated kinase modification," *J. Biol. Chem.*, Mar. 2007; 282(9):6075-89.
Yin et al., "In vitro and in vivo Evaluation of the Antitumor Efficiency of Resveratrol Against Lung Cancer," *Asian Pacific J Cancer Prev.*, Mar. 2013; 14(3):1703-1706.
Zakeri et al., "The Study of Cell Death by the Use of Cellular and Developmental Models," In *When Cells Die: A Comprehensive Evaluation of Apoptosis and Programmed Cell Death*, New York: Wiley-Liss. 1998; 97-129.
Zhao et al., "Origin of the cis-Effect: a Density Functional Theory Study of Doubly Substituted Ethylenes," *Acta Phys.-Chim. Sin.*, Jan. 15, 2013; 29(1):43-54.
Zhao et al., "Clinical efficacy and safety of traditional Chinese medicine combined with Western Medicine in patients with diabetic acute ischemic stroke," *J. Tradit. Chin. Med.*, Apr. 15, 2014; 34(2):145-9.
International Search Report and Written Opinion PCT/US2015/051424, dated Dec. 17, 2015, 12 pgs.
International Preliminary Report on Patentability PCT/US2015/051424, dated Apr. 6, 2017, 10 pgs.

\* cited by examiner

A cis-Gnetin H / A549 trans-Gnetin H / BT20 cis-Gnetin H / BT20 trans-Gnetin H / BT20

B

CIS-GNETIN H AND TRANS-GNETIN H AS THERAPEUTIC AGENTS

CONTINUING APPLICATION DATA

This is a continuation application of U.S. patent application Ser. No. 15/513,375, filed Mar. 22, 2017, which is the § 371 U.S. National Stage of International Application No. PCT/US2015/051424, filed Sep. 22, 2015, which claims the benefit of U.S. Provisional Application Ser. No. 62/053,497, filed Sep. 22, 2014, each of which is incorporated herein by reference in its entirety.

BACKGROUND

Resveratrol (3,5,4'-trihydroxystilbene) is a naturally occurring phenylpropanoid produced in a number of plant species, such as grapevines, berries, peanuts, and Japanese knotweeds (Aggarwal et al., Anticancer Res., 2004; 24:2783-2840). Resveratrol has been intensively studied over the past decade and shown to possess anti-tumor potential in a wide variety of human tumor cells and various animal models (Bishayee, Cancer Prev. Res. 2009; 2:409-418). Resveratrol has potential anti-cancer and anti-inflammatory effects (Aggarwal et al., 2004, Anticancer Res., 24:2783-840; Aggarwal et al., 2004, Anticancer Res., 24:2783-840; Manna et al., 2000, J. Immunol., 164:6509-19).

cis-gnetin H and trans-gnetin H are trimers of resveratrol, differing from each other in the olefinic moiety between C-7'/C-8' (FIGS. 1A and 1B; He et al., Chem. Pharm. Bull. 2010; 58:843-847). These oligostilbenes as well as other resveratrol derivatives can be obtained from the seeds of *Paeonia suffruticosa* (He et al., Chem. Pharm. Bull. 2010; 58:843-847). *Paeonia suffruticosa* has been widely used in traditional Chinese medicine as an analgesic, anti-anaphylactic, anti-oxidative, and anti-inflammatory agent (He et al., Chem. Pharm. Bull. 2010; 58:843-847; Hu et al., J. Ethnopharmacol., 2010, 128:100-6; Oh et al., J. Ethnopharmacol., 2003, 84:85-9). The seeds of the plant contain multiple stilbenes that showed potential cytotoxic, anti-mutagenic, ecdysteroid antagonist, anti-oxidant, hyperpigmentation, antitumor, and anti-inflammatory activity, and have been used in traditional medicine throughout East Asia to treat conditions and diseases such as atherosclerosis, inflammation, infection, and cutaneous diseases (Choi et al., J. Biomed. Sci., 2012, 19:82; Gao et al., J. Ethnopharmacol., 2015, 169:24-33; He et al., Chem. Pharm. Bull. 2010; 58:843-847).

While there are numerous studies on the bioactivities of resveratrol, little is known about the biological role of cis-gnetin H or trans-gnetin H. In vitro studies using HL-60 (human leukemia), C6 (mouse glioma), Hela (human cervicse), MCF-7 (human breast) and L1210 (mouse leukemia) cell lines suggested that trans-gnetin H has anti-tumor activity (Kim et al., Arch. Pharm. Res. 2002; 25:293-299; Ha et al., Arch. Pharm. Res. 2009; 32:177-83) but trans-gnetin H's potential as a cancer chemopreventive has not been clearly elucidated. Additionally, the anti-inflammatory mechanisms of *Paeonia suffruticosa* have not been fully characterized.

SUMMARY OF THE INVENTION

The invention identifies cis-gnetin H and trans-gnetin H as novel therapeutic agents for the treatment and prevention of various diseases and conditions. In one aspect, the invention provides compositions and methods for treating or preventing cancer or a precancerous condition in a subject. A composition comprising an effective amount of cis-gnetin H and/or trans-gnetin H, or a derivative thereof is administered to a subject afflicted with or at risk for cancer or a precancerous condition. A preferred therapeutic agent for the treatment or prevention of cancer or a precancerous condition in a subject is cis-gnetin H. The cancer or precancerous condition can involve any tissue or organ, without limitation, such as bone, brain, breast, cervix, larynx, lung, pancreas, prostate, skin, spine, stomach, uterus or blood. The cancer can be a bone cancer, brain cancer, breast cancer, cervical cancer, cancer of the larynx, lung cancer, pancreatic cancer, prostate cancer, skin cancer, cancer of the spine, stomach cancer, uterine cancer, or a blood cancer. The cancer can be a metastatic cancer.

In another aspect, the invention provides compositions and methods for inhibiting the growth of a tumor in a subject. A composition comprising an effective amount of cis-gnetin H, trans-gnetin H, and/or a derivative thereof is administered to a subject who is afflicted with a tumor. A preferred therapeutic agent for the inhibiting the growth of a tumor in a subject is cis-gnetin H. The tumor may include, without limitation, a solid tumor present in the bone, brain, breast, cervix, larynx, lung, pancreas, prostate, skin, spine, stomach, or uterus of the subject. The tumor may be a fast growing tumor.

In yet another aspect, the invention provides compositions and methods for treating or preventing inflammation in a subject. A composition comprising an effective amount of cis-gnetin H, trans-gnetin H, and/or a derivative thereof is administered to a subject who is at risk of or experiencing inflammation. Examples of inflammatory conditions that can be treated, managed, or prevented include autoimmune and inflammatory diseases such as rheumatoid arthritis and inflammatory bowel disease.

The composition used in the methods of the invention may include either or both cis- and trans-gnetin H, and/or derivatives thereof. cis-gnetin H or trans-gnetin H may be at least 50%, 60%, 70%, 80%, 90%, 95%, or 99% of the total cis- and trans-gnetin H in the composition. The composition may include an extract prepared from *Paeonia suffruticosa* seeds. Optionally, the composition further includes a pharmaceutically acceptable carrier. In some embodiments, the composition may further include an additional active agent, such as an anticancer agent, antiangiogenic agent, a chemopreventive agent, an anti-inflammatory agent, a cytokine, a chemokine, a therapeutic antibody, an immunogen, an antigen, an adjuvant, or an antioxidant, an immunomodulatory compound, a biologic compound, an antineoplastic agent, or a chemotherapeutic agent. Preferably, at least one additional active agent is a non-naturally occurring compound.

In another aspect, the invention includes cis-gnetin H, trans-gnetin H, and/or derivatives thereof for use as a therapeutic agent, including use in the treatment or prevention of cancer or a precancerous condition, use in inhibiting or reversing the growth of a tumor, or use in the treatment or prevention of inflammation. Use of cis-gnetin H, trans-gnetin H, and/or derivatives thereof for preparation of a medicament for the treatment or prevention of cancer or a precancerous condition, or for inhibiting the growth of a tumor, or for treatment or prevention of inflammation, is also included in the invention.

In another aspect, the invention includes a plant extract that includes cis-gnetin H and/or trans-gnetin H for use as a therapeutic agent, including a plant extract that includes cis-gnetin H and/or trans-gnetin H for use in the treatment or prevention of cancer or a precancerous condition, or for use in inhibiting the growth of a tumor, or for use in the treatment or prevention of inflammation. Use of a plant extract including cis-gnetin H and/or trans-gnetin H for preparation of a medicament for the treatment or prevention of cancer or a precancerous condition, or for inhibiting the growth of a tumor, or for the treatment or prevention of inflammation, is also included in the invention. In some embodiments, the plant extract is prepared from *Paeonia suffruticosa* seeds.

DESCRIPTION OF ILLUSTRATIVE EMBODIMENTS

Figure 1:
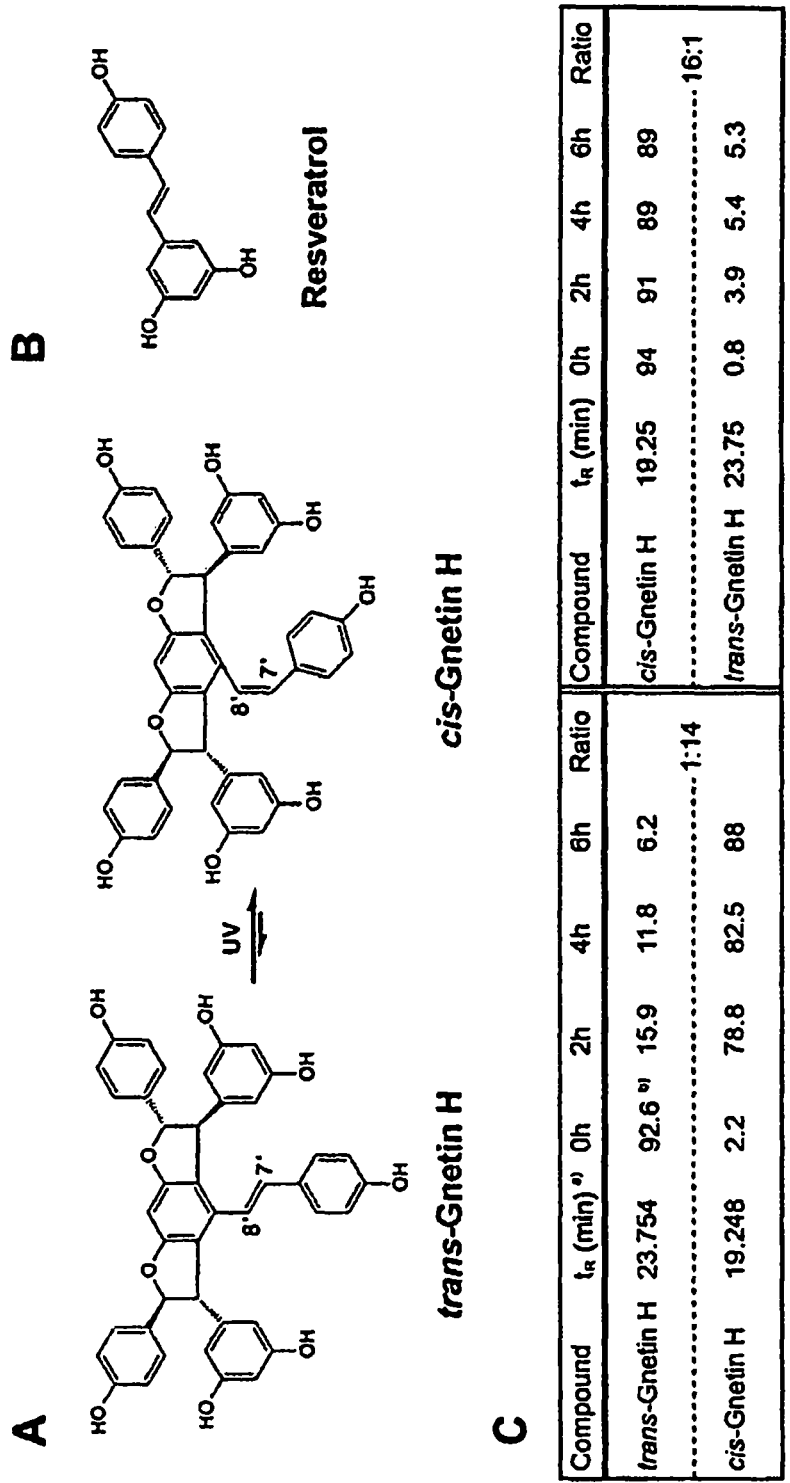
FIG. 1 shows structures of cis-gnetin H and trans-gnetin H compared to resveratrol, and conversion of trans-gnetin H and cis-gnetin H with UV-irradiation. A, Structures of trans- and cis-gnetin H. B, Structure of resveratrol. C, Conversion rate of trans- and cis-gnetin H when individually illuminated by a 12-watt fluorescent lamp for 2, 4 and 6 hours.

The present invention provides compounds, compositions and methods relating to cis-gnetin H and/or trans-gnetin H, including modifications, derivatives and conjugates thereof, and their use as a prophylactic or therapeutic agent, for example, to prevent or treat the cancers or precancerous conditions, to inhibit, slow or reverse the growth of tumors, or to prevent or treat inflammation, autoimmune disease and/or inflammatory disease. cis-gnetin H and trans-gnetin H can be isolated or extracted from naturally occurring sources or can be chemically or enzymatically synthesized. cis-gnetin H and/or trans-gnetin H can be administered alone or in combination with other therapeutics via a variety of routes of administration.

We have found that cis-gnetin H and trans-gnetin H have significant potential as anticancer agents. For example, we have shown that cis-gnetin H can prevent the growth of bone, breast and lung cancer cell lines with IC50 values ranging from 2.80-10.04 μM. In a mouse xenograft lung tumor model, cis-gnetin H worked as well as the routinely utilized anticancer agent, staurosporine, and was significantly better at reducing the sizes of large tumors. We have also shown that cis-gnetin H is the more stable of the two isomers and that trans-gnetin H is converted to cis-gnetin H by photooxidation. Further, based upon the results shown in Example 1, cis-gnetin H is expected to show less toxicity than other commonly employed chemotherapeutic agents, such as staurosporine and 5-fluorouracil (see Example 1 and, for example, Cyr et al., Anticancer Res. 28: 2753-2764 (2008)). Lower toxicity allows cis-gnetin H to be administered at higher doses than other chemotherapeutic agents.

We have also found that that cis-gnetin H and trans-gnetin H have significant potential as immunomodulatory agents. For example, we have shown that cis- and trans-gnetin H significantly inhibited cytokine responses without affecting cell viability. cis- and trans-gnetin H also effectively inhibited the nuclear translocation of p65 and inhibited the phosphorylation of IKK-β, IκB α, as well as p65. cis- and trans-gnetin H may exert anti-inflammatory or immunomodulatory effects by suppressing the key signaling molecule involved in the NF-κB pathway.

Cis-Gnetin H and Trans-Gnetin H cis-gnetin H and trans-gnetin H are resveratrol trimers, originally thought to exist in only one form, trans-gnetin H, previously referred to in the art simply as "gnetin H." See He et al., Chem. Pharm. Bull. 58(6) 843-847 (2010); Kim et al., Arch. Pharm. Res. 25(3):293-9 (002); Choi et al., Planta Med. 77:374-376 (2011). The structures are shown below:

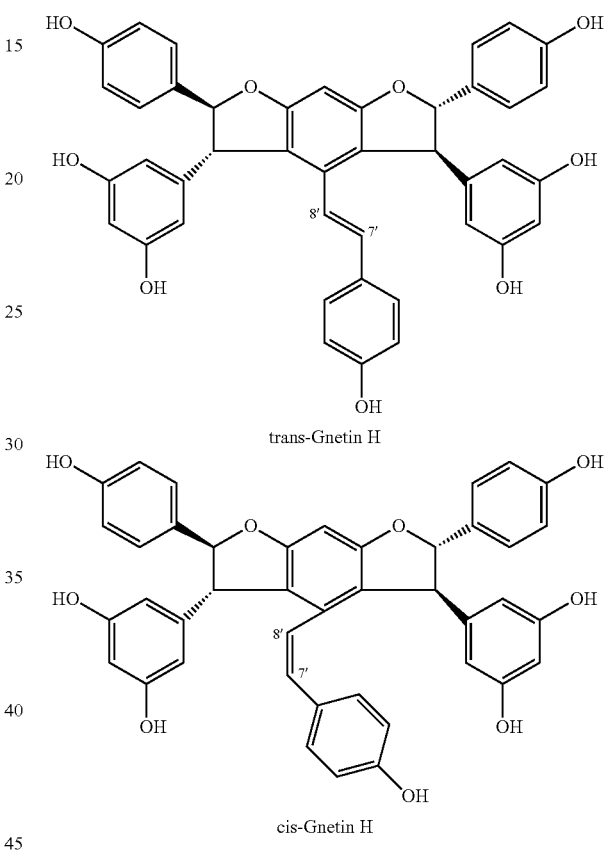

Under photooxidation conditions, trans-gnetin H converts to cis-gnetin H. Surprisingly, cis-gnetin H was found to be more stable than trans-gnetin H. This increased stability allows for easier storage, transport, formulation, and administration. Because it is more stable, the cis form may also prove to be easier to synthesize.

The invention includes purified and partially purified forms of cis-gnetin H and trans-gnetin H, as well as crude plant extracts that contain cis-gnetin H and/or trans-gnetin H.

Also included in the invention are synthetic derivatives of cis-gnetin H and trans-gnetin H. Derivatives include, but are not limited to, alkylated (e.g., methylated), hydroxylated, sulfated and amino derivatives of cis-gnetin H and trans-gnetin H.

It is known that the biological activities of cis- and trans-isomers of naturally occurring compounds may differ (see, e.g., Zhao et al., Acta Phys.-Chim. Sin. 2013, 29(1), 43-54; Anisimova et al., Chem. Cent. J. 2011, 5:88; Pettit et al., J. Nat. Prod., 72:1637-1642)); thus, it was not known in advance whether cis-gnetin H would exhibit the anti-cancer and anti-tumor properties described in Example I. Moreover, not all naturally occurring stilbenes or their derivatives have anti-cancer or anti-tumor activity. See, for example Kim et al., Arch. Pharm. Res. 25(3) 293-299 (2002), and Kim et al., Biosci. Biotechnol. Biochem., 66(9): 1990-1993 (2002). Additionally, it was not known in advance whether either or both isomers would exhibit the anti-inflammatory or immunomodulatory properties described Example 3.

Isolation or Synthesis of Cis-Gnetin H and Trans-Gnetin H cis-gnetin H and trans-gnetin H can be extracted and/or isolated from peony plants (genus *Paeonia*), including but not limited to *Paeonia suffruticosa, Paeonia lactiflora,* or *Paeonia anamola.* cis-gnetin H and trans-gnetin H can also be found in other plants, such as the leaf and stem of *Vitis amurensis*, also known as the Amur grape. Any convenient plant part can serve as a source of cis-gnetin H and trans-gnetin H including, without limitation, the seeds, leaves, stems, roots, or flowers. In a preferred embodiment, cis-gnetin H and/or trans-gnetin H obtained from a root or seed extract of *Paeonia suffruticosa* or *Paeonia lactiflora.* cis-gnetin H can be produced from photochemical transformation of trans-gnetin H. For example, trans-gnetin H can be photooxidized for at least 30 minutes, 45 minutes, 60 minutes, 90 minutes, 2 hours, 3 hours, 4 hours, 5 hours, 6 hours, 7 hours, 8 hours, 9 hours, 10 hours, 12 hours, 24 hours, 48 hours, or 72 hours. Photooxidation can take place with light source such as a fluorescent lamp and optionally a photoactivating compound.

It is expected that cis-gnetin H and trans-gnetin H can be enzymatically synthesized using the appropriate plant enzymes. In one embodiment, resveratrol may be a starting material. Optionally, a stilbene synthase can be used, and additional co-factors can also be introduced, including but not limited to, malonyl-coenzyme A (CoA) and p-coumaroyl-CoA (Aggarwal et al., 2004, Anticancer Res. 24:2783-2840).

Pharmaceutical Compositions

The present invention also provides a pharmaceutical composition that includes, as an active agent, at least one of cis-gnetin H, trans-gnetin H, a synthetic derivative thereof, or a combination thereof, and a pharmaceutically acceptable carrier. The active agent is formulated in a pharmaceutical composition and then, in accordance with the method of the invention, administered to a subject, such as a human or veterinary subject, in a variety of forms adapted to the chosen route of administration. The formulations include, but are not limited to, those suitable for oral, rectal, vaginal, topical, nasal, ophthalmic or parental (including subcutaneous, intramuscular, intraperitoneal, intratumoral, and intravenous) administration.

The pharmaceutically acceptable carrier can include, for example, an excipient, a diluent, a solvent, an accessory ingredient, a stabilizer, a protein carrier, or a biological compound. Nonlimiting examples of a protein carrier includes keyhole limpet hemocyanin (KLH), bovine serum albumin (BSA), ovalbumin, or the like. Nonlimiting examples of a biological compound which can serve as a carrier include a glycosaminoglycan, a proteoglycan, and albumin. The carrier can be a synthetic compound, such as dimethyl sulfoxide or a synthetic polymer, such as a polyalkyleneglycol. Ovalbumin, human serum albumin, other proteins, polyethylene glycol, or the like can be employed as the carrier. In a preferred embodiment, the pharmaceutically acceptable carrier includes at least one compound that is not naturally occurring or a product of nature.

In some embodiments, the active agent cis-gnetin H, trans-gnetin H, and/or synthetic derivative thereof is optionally formulated in combination with one or more additional active agents. In some embodiments, the pharmaceutical composition of the invention contains a first active agent that includes cis-gnetin H, trans-gnetin H, and/or a synthetic derivative thereof, and a second active agent that can include one or more of, for example, an anticancer agent, antiangiogenic agent, a chemopreventive agent, an anti-inflammatory agent, a cytokine, a chemokine, a therapeutic antibody, an immunogen, an antigen, an adjuvant, or an antioxidant, an immunomodulatory compound, a biologic compound, an antineoplastic agent, or a chemotherapeutic agent. More generally, any known therapeutic or prophylactic agent can be included as additional active agent. The action of the additional active agent in the combination therapy can be cumulative to the cis-gnetin H, trans-gnetin H or it can be complementary, for example to manage side effects or other aspects of the patient's medical condition.

An exemplary multicomponent composition is a vaccine. A vaccine contains at least one immunogenic or antigenic component, and a pharmaceutically acceptable carrier. Optionally, a vaccine includes one or more adjuvants. cis-gnetin H, trans-gnetin H, and/or a derivative thereof can be included in a vaccine composition to ameliorate, reduce, or eliminate a reactogenic inflammatory response in the subject to whom the vaccine is administered. Inclusion of cis-gnetin H, trans-gnetin H, and/or derivatives thereof in vaccine formulations may reduce reactogenicity, particularly in live virus vaccines. See Athearn et al., PLoS One. 2012; 7(10): e46516. doi: 10.1371/journal.pone.0046516. Epub 2012 Oct. 8; Lewis et al., J Immunol Res. 2015; 2015:909406. Epub 2015 Aug. 25). More generally, cis-gnetin H, trans-gnetin H, and/or derivatives thereof can be co-administered with therapeutic agents that might otherwise trigger inflammation, particularly in sensitive, ill or vulnerable individuals, such as the very young or very old, in order to reduce the extent of the inflammatory response.

A pharmaceutical composition of the invention preferably includes at least one compound that is not naturally occurring or a product of nature. In a particularly preferred embodiment, the pharmaceutical composition includes at least one non-naturally occurring therapeutic or prophylactic agent.

In some embodiments, the pharmaceutical composition contains purified cis-gnetin H and/or trans-gnetin H or a derivative thereof; in other embodiments, the pharmaceutical composition can contain a partially purified plant extract that contains cis-gnetin H and/or trans-gnetin H.

The formulations may be conveniently presented in unit dosage form and may be prepared by any of the methods well-known in the art of pharmacy. All methods include the step of bringing the active agent into association with a pharmaceutical carrier. In general, the formulations are prepared by uniformly and intimately bringing the active compound into association with a liquid carrier, a finely divided solid carrier, or both, and then, if necessary, shaping the product into the desired formulations.

Formulations of the present invention suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into sustained-release preparations and devices.

Formulations suitable for parenteral administration conveniently include a sterile aqueous preparation of the active agent, or dispersions of sterile powders of the active agent, which are preferably isotonic with the blood of the recipient. Parenteral administration of cis-gnetin H and/or trans-gnetin H (e.g., through an I.V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration can be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

Administration of Cis-Gnetin H and Trans-Gnetin H

The active agents cis-gnetin H, trans-gnetin H, and/or synthetic derivatives thereof can be administered to a subject alone or in a pharmaceutical composition that includes the active agent and a pharmaceutically acceptable carrier. cis-gnetin H and/or trans-gnetin H, or derivatives thereof, can be introduced into the subject either systemically or at the site of a cancer tumor or inflammation. The active agent is administered to a human or animal subject, including a domestic or domesticated mammal or other animal, in an amount effective to produce the desired effect. cis-gnetin H and/or trans-gnetin H, or derivatives thereof, can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Local administration can include topical administration, administration by injection, or perfusion or bathing of an organ or tissue, for example.

The formulations can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

In some embodiments, a mixture of the cis/trans isomers, cis-gnetin H and trans-gnetin H, or derivatives thereof, can be administered to a subject. For example, the extracted, isolated, purified, or synthesized cis-gnetin H can be present in a mixture that also includes trans-gnetin H, such that cis-gnetin H is at least 50% of the total cis- and trans-gnetin H, more particularly at least 60%, 70%, 80%, 85%, 90%, 95%, or 99% of the total cis- and trans-gnetin H. Analogously, the extracted, isolated, purified, or synthesized trans-gnetin H can be present in a mixture that also includes cis-gnetin H, such that trans-gnetin H is at least 50% of the total cis- and trans-gnetin H, more particularly at least 60%, 70%, 80%, 85%, 90%, 95%, or 99% of the total cis- and trans-gnetin H. The relative amounts of cis- and trans-isomers in the mixture may be specified based upon the prophylactic or therapeutic use of the resulting compositions. The relative amounts of cis-gnetin H and total cis- and trans-gnetin H can be measured by high-performance liquid chromatography (HPLC). In other embodiments, cis-gnetin H that is administered to a subject can be substantially or completely free of trans-gnetin H; or trans-gnetin H that is administered to a subject can be substantially or completely free of cis-gnetin H.

Dosage levels of the active agent, including but not limited to cis-gnetin H, in the pharmaceutical compositions of this invention can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the cis- and/or trans-gnetin H, or derivatives thereof; the age, sex, weight, condition, general health and prior medical history of the subject being treated, and like factors well known in the medical arts.

Dosages and dosing regimens that are suitable for resveratrol and other stilbenoids are likewise suitable for therapeutic or prophylactic administration of cis-gnetin H and/or trans-gnetin H or derivatives thereof. For example, purified cis-gnetin H and/or trans-gnetin H or derivatives thereof, can be administered orally in an amount of between 10 mg and 100 mg per day, as a medication, nutritional supplement, or food additive. As another example, cis-gnetin H and/or trans-gnetin H, or derivatives thereof, can be administered in dosages ranging from 0.01 mg/kg to 10 mg/kg body weight, or higher; or in a form sufficient to provide a daily dosage of 0.03 mg/kg body weight to about 10 mg per/kg body weight of the subject to which it is to be administered. See, e.g., US Pat. Publ. 20080262081 for nutraceutical compositions, dosing information and methods relating to resveratrol that are equally applicable to cis-gnetin H and/or trans-gnetin II, or derivatives thereof.

cis-gnetin H and/or trans-gnetin H, or derivatives thereof, can also be administered as an extract obtained from a plant source, such as a seed. Dosages and dosing regimens that are suitable for melinjo seed extract and other seed extracts are likewise suitable for therapeutic prophylactic administration of plant extracts containing cis-gnetin H and trans-gnetin H. For example, between 20 and 1000 mg/day can be administered as a powdered extract in loose, capsule or tablet form. See, e.g., Konno et al., Evidence-Based Complementary and Alternative Medicine, Volume 2013 (2013), Article ID 589169, 9 pages; http://dx.doi.org/10.1155/2013/589169; Tani et al., J. Agric. Food Chem, 62(8):1999-2007 (2014).

A physician having ordinary skill in the art can readily determine and prescribe the effective amount of the pharmaceutical composition required. For example, the physician could start doses of cis-gnetin H and/or trans-gnetin H, or derivatives thereof, utilized in the pharmaceutical composition at levels lower than that required in order to achieve the desired therapeutic effect and gradually increase the dosage until the desired effect is achieved.

Anti-Tumor/Anti-Cancer Activity and Related Methods trans-gnetin H has been shown by others to inhibit the growth of various tumor cell lines, but the efficacy of cis-gnetin H against tumor cell lines was unknown prior to the present work. Additionally, neither trans-gnetin H nor cis-gnetin H has, to our knowledge, been evaluated in any animal studies until now. Example I demonstrates that cis-gnetin H and trans-gnetin H have significant anticancer activity.

The invention therefore provides a method for treating or preventing cancer or a precancerous condition in a subject, and/or inhibiting or reversing tumor growth in a subject, by administering to a subject a composition comprising cis-gnetin H, trans-gnetin H and/or a derivative thereof, in an amount effective to treat or prevent the cancer or precancerous condition, or inhibit or reverse growth of the tumor. Administration of the composition can be performed before, during, or after a subject develops cancer, a precancerous condition or a tumor.

In one embodiment, the method is a therapeutic method for treating a subject suffering from a cancer or a precancerous condition by administering cis-gnetin H, trans-gnetin H, and/or derivatives thereof, to the subject in an amount effective to treat the cancer or precancerous condition. In another embodiment, the therapeutic method includes administering cis-gnetin H trans-gnetin H, and/or derivatives thereof, to a subject who has a tumor, in an amount effective to inhibit, slow, or reverse growth of the tumor. Therapeutic treatment is initiated after the development of cancer, a precancerous condition, or a tumor. Treatment initiated after the development of cancer may result in decreasing the severity of the symptoms of one of the conditions, or completely removing the symptoms. Advantageously, cis-gnetin H is particularly well-suited for the treatment of fast-growing tumors and metastatic cancers.

In another embodiment, cis-gnetin H, trans-gnetin H, and/or derivatives thereof are administered prophylactically, e.g., as a chemopreventive agent, in an amount effective to prevent or delay the development of cancer or a precancerous condition in a subject. Treatment that is prophylactic, for instance, can be initiated before a subject develops cancer or manifests cancer symptoms. An example of a subject that is at particular risk of developing cancer is a person having a risk factor, such as a genetic marker, that is associated with the disease. Examples of genetic markers indicating a subject has a predisposition to develop certain cancers include alterations in the BRAC1 and/or BRAC2 genes (breast, prostate, or colon cancer) and HPC1 (prostate cancer).

The method of the invention can be used to treat a variety of cancerous or precancerous conditions, including tumors or dysplasia. A tumor can be a solid tumor, such as a carcinoma, a sarcoma, or a lymphoma, and can be present, for example, in the bone, brain, breast, cervix, larynx, lung, pancreas, prostate, skin, spine, stomach, or uterus. The cancer treated by the method of the invention can also be a blood cancer, such as a leukemia. The dysplasia can be an epithelia dysplasia. The tumor can made up of tumor cells, including lymphoid and myeloid cancers; multiple myeloma; cancers of the bone, breast, prostate, stomach, colon, pancreas, and thyroid; melanoma; head and neck squamous cell carcinoma; ovarian carcinoma; and cervical carcinoma.

Administration of cis-gnetin H, trans-gnetin H, and/or derivatives to treat or prevent cancer, a precancerous condition, or to inhibit or reverse tumor growth, thereof can occur before, during, and/or after other treatments. Such combination therapy can involve the administration of cis-gnetin H, trans-gnetin H, and/or derivatives thereof before, during and/or after the use of other anti-cancer agents, for example, chemotherapeutic agents or radiation or both. It is expected that cis-gnetin H, trans-gnetin H, and/or derivatives thereof may potentiate the effects of cytokines, chemotherapeutic agents, or gamma radiation (see, e.g., Aggarwal et al., Anticancer Research, 2004; 24:2783-2840). The administration of cis-gnetin H, trans-gnetin H, and/or derivatives thereof can be separated in time from the administration of additional anti-cancer agents or other therapeutic agents by hours, days, or even weeks; alternatively, they can be administered concurrently, either together in the same composition or in separate compositions. Additionally or alternatively, the administration of cis-gnetin H, trans-gnetin H, and/or derivatives thereof can be combined with other biologically active agents or modalities such as, but not limited to, an antineoplastic agent, and non-drug therapies, such as, but not limited to, surgery. A preferred method involves the administration of cis-gnetin H which is shown in Example 1 to be a more potent anticancer agent than its stereoisomer, trans-gnetin H.

Anti-Inflammatory Activity and Related Methods

Chronic inflammation is known to be associated with a wide variety of diseases and disorders, for example autoimmune disease such as rheumatoid arthritis (RA) and inflammatory bowel disease (IBD), obesity, diabetes, infectious diseases, inflammatory atherosclerosis, cancer, depression, heart disease, stroke, and Alzheimer's Disease. Inflammation can be chronic or acute; systemic or localized; autoimmune or associated with an infection caused by an exogenous agent. An autoimmune response is generally characterized as an immune response directed against a self-antigen. Inflammation caused by an exogenous agent, on the other hand, includes inflammation caused by an infectious agent or a pathogen such as a virus, bacteria, fungus, protist, plant, or other organism. Pathogenic bacteria known to induce a chronic inflammatory response include *Chlamydophila pneumoniae* and *Porphyromonas gingivalis* (http://www.bumc.bu.edu/gencolab/research/pathogen-induced-chronic-inflammatory-disorders/)

Inflammatory conditions and autoimmune diseases can be treated or prevented using immunomodulators or biologics, or both. Immunomodulators are compounds that weaken or modulate the activity of the immune system, which may in turn decrease the inflammatory response. Immunomodulators are used in organ transplantation to prevent rejection of the new organ, and to treat or manage autoimmune diseases such as rheumatoid arthritis and inflammatory bowel disease, which appears to be caused by an overactive immune system. Exemplary immunomodulators include azathioprine (available under the tradenames IMURAN and AZASAN), 6-mercaptopurine (6-MP, available under the tradename PURINETHOL), cyclosporine A (available under the tradenames SANDIMMUNE and NEORAL), tacrolimus (available under the tradename PROGRAF), and methotrexate (amethopterin, available under the tradenames MTX, RHEUMATREX, and MEXATE) are exemplary immunomodulators. However immunomodulators are known to be accompanied by numerous side effects, including headache, nausea, vomiting, diarrhea, and malaise (general feeling of illness), pancreatitis (inflammation of the pancreas), bone marrow suppression, which may increase the risk of infection or serious bleeding, decreased kidney function, hepatitis, diabetes, increased cholesterol levels, sleep problems, mild tremor, high blood pressure, swollen gums, tingling of the fingers and feet, increased facial hair, and increased risk of lymphoma (a cancer of the lymphatic system), low white blood cell count, scarring of the liver and lung inflammation.

Whereas immunomodulators decrease the body's immune response, which appears to be responsible causing the inflammation and damage associated with it, biologics are genetically engineered drugs that specific target proteins or other molecules involved in the inflammatory process. For example, certain biologics block tumor necrosis factor-alpha, or TNF-α. TNF-α is an inflammatory cytokine that is present in elevated levels in diseases such as inflammatory bowel disease, and plays a central role in the inflammatory response and damage to the GI tract that leads to symptoms. These biologics neutralize TNF-α's ability to cause inflammation. Biologics also have serious side effects, however, such as increased risk of mild to severe infection—from the common cold to tuberculosis (TB) and hepatitis B, and increased risk of certain types of lymphoma, non-melanoma skin cancer, a lupus-like reaction, and exacerbation of pre-existing heart failure. Three of the most widely used medications, infliximab (available under the tradename REMICADE), adalimumab (available under the tradename HUMIRA) and etanercept (available under the tradename ENBREL) are antibodies (a type of "biologic" drug) that act by binding to the cytokine tumor necrosis factor (TNF-α). Unfortunately all three drugs come with a FDA black box warning and have caused numerous problems and even death in patients. Moreover, these drugs also only block the action of one cytokine (TNF-α). Other biologics in current use for management of conditions such as rheumatoid arthritis or inflammatory bowel disease include tocilizumab (available under the tradename ACTEMRA) certolizumab pegol (available under the tradename CIMZIA), anakinra (available under the tradename KINERET), abatacept (available under the tradename ORENCIA) rituximab (available under the tradename RITUXAN) and golimumab (available under the tradename SIMPONI). There is therefore a clear need for safe immunomodulatory agents for treating autoimmune diseases such as rheumatoid arthritis and inflammatory bowel disease.

It has been found that both cis- and trans-gnetin H can act as immunomodulators for treating or preventing immune-based diseases or conditions, including autoimmune disease. Example 3 demonstrates that cis-gnetin H and trans-gnetin H have significant anti-inflammatory activity. Moreover, cis- and trans-gnetin H act at a much earlier step in the cytokine pathway than the biologics in current use, and block the release of multiple cytokines, a clear advantage over these biologics. Example 3 shows that trans-gnetin H may be preferred as an immunomodulator over its stereoisomer cis-gnetin H; however, either or both compounds, or their derivatives, are suitable for use as an immunomodulator.

Compositions that include cis-gnetin H, trans-gnetin H and/or derivatives thereof can thus be used to prevent, inhibit, treat, or control inflammation. These compositions are useful to treat a variety of diseases, disorders, and conditions characterized by or associated with inflammation, including but not limited to autoimmune diseases.

Accordingly, the invention provides a method for treating or preventing inflammation and/or autoimmune disease in a subject by administering to a subject a composition comprising cis-gnetin H, trans-gnetin H and/or a derivative thereof, in an amount effective to treat or prevent inflammation and/or autoimmune disease Administration of the composition can be performed before, during, or after a subject develops an inflammatory condition or autoimmune disease, or manifests inflammation or symptoms of inflammation or autoimmune disease.

In one embodiment, the method is a therapeutic method for treating a subject suffering from inflammation and/or autoimmune disease by administering cis-gnetin H, trans-gnetin H, and/or derivatives thereof, to the subject in an amount effective to treat the inflammation or autoimmune disease. Therapeutic treatment is initiated after the development of inflammation and/or autoimmune disease. Treatment initiated after the development of an inflammatory condition or autoimmune disease, or after manifestation of inflammation or symptoms of inflammation, may result in decreasing the severity of the symptoms of one of the conditions, or completely removing the symptoms.

In another embodiment, cis-gnetin H, trans-gnetin H, and/or derivatives thereof are administered prophylactically in an amount effective to prevent or delay the development of inflammation and/or autoimmune disease in a subject. Treatment that is prophylactic, for instance, can be initiated before a subject develops an inflammatory condition or autoimmune disease, or manifests inflammation or symptoms of inflammation or autoimmune disease. An example of a subject who is at particular risk of developing inflammation or autoimmune disease is a person having a risk factor, such as a genetic marker, that is associated with inflammatory disease or autoimmune disease, or a person who has recently received a transplant. Another example is a subject who is suffering from a disease associated with inflammation, but who has not developed an inflammatory response.

Examples of diseases, disorders or conditions that can be treated or prevented by the composition of the invention include, without limitation, rheumatoid arthritis (RA), inflammatory bowel disease (IBD) including Crohn's disease and ulcerative colitis, idiopathic orbital inflammation, plaque psoriasis, psoriatic arthritis, ankylosing spondylitis, juvenile idiopathic arthritis, lupus, myasthenia gravis, focal segmental glomerulosclerosis, macrophage activation syndrome, non-Hodgkin's lymphoma, chronic lymphoid leukemia, precursor lymphoblastic lymphoma, familial Mediterranean fever (FMF), neonatal onset multisystem inflammatory disease (NOMID), tumor necrosis factor receptor-associated periodic syndrome (TRAPS), deficiency of the interleukin-1 receptor antagonist (DIRA), and Behçet's disease.

Additional inflammatory disorders that can be treated or prevented using the method of the invention include, for example, transplant rejection, graft vs. host disease, asthma, allergic reactions, chronic prostatitis, pelvic inflammatory disease, glomerulonephritis, reperfusion injury, and vasculitis; others include obesity, diabetes, infectious diseases, cancer, depression, heart disease, stroke, and Alzheimer's Disease. Diseases, conditions or disorders characterized by inflammation may include the suffix "itis," and it is expected that any disease, disorder, or condition having "itis" as part of its name can be treated or prevented using the composition of the invention. Inflammation also plays an important role in the pathogenesis of atherosclerosis. The link between rheumatoid arthritis and an increased risk of cardiovascular disease and mortality is well established. Thus, cis-gnetin H, trans-gnetin H and derivatives thereof are useful for treating cardiovascular disease associated with or caused by other inflammatory conditions.

Administration of cis-gnetin H, trans-gnetin H, and/or derivatives thereof can occur before, during, and/or after other treatments. Such combination therapy can involve the administration of cis-gnetin H, trans-gnetin H, and/or derivatives thereof before, during and/or after the use of other anti-inflammatory agents, for example, non-steroidal anti-inflammatory drugs, corticosteroids, TNF-α blockers, and other active agents as described herein for cumulative therapy or reduction or elimination of side effects. In a particularly preferred embodiment, the invention contemplates combination therapy that employs, in addition to cis-gnetin H, trans-gnetin H, and/or a derivative thereof, one or more immunomodulators and/or one or more biologics to treat patients with autoimmune diseases such as rheumatoid arthritis (RA) and inflammatory bowel disease (IBD), including Crohn's disease and ulcerative colitis. The therapeutic and prophylactic methods of the invention therefore encompass administration of a pharmaceutical composition that contains a first active agent that includes, as an immunomodulatory compound, cis-gnetin H, trans-gnetin H, and/or a synthetic derivative thereof, and a second active agent that includes at least one of an immunomodulatory compound (in addition to the cis-gnetin H, trans-gnetin H, and/or a synthetic derivative thereof) and/or a biologic compound. The second active agent include one or more compounds selected from, without limitation, azathioprine, 6-mercaptopurine, cyclosporine A, tacrolimus, methotrexate, amethopterin, prednisone, prednisolone, infliximab, adalimumab, etanercept, tocilizumab, certolizumab pegol, anakinra, abatacept, rituximab, and golimumab.

The administration of cis-gnetin H, trans-gnetin H and/or derivatives thereof can be separated in time from the administration of other active agents, such as additional immunomodulatory agents and/or biologics, by hours, days, or even weeks; alternatively, the other active agents can be administered concurrently, either together in the same composition or in separate compositions. Additionally or alternatively, the administration of cis-gnetin H, trans-gnetin H and/or derivatives thereof can be combined with other biologically active agents or modalities such as, for example, anti-inflammatory chemotherapeutic agents, and non-drug therapies, such as, but not limited to, radiotherapy, heat therapy, cryotherapy, electrical therapy, massage, and acupuncture.

Compositions and Methods for Veterinary Use

Any of the compositions or methods described herein that include cis-gnetin H, trans-gnetin H, and/or derivatives thereof can be used in veterinary applications. Veterinary uses in domestic or domesticate animals (including small animals such as cats, dogs, and other pets, as well as large animals such as cows, horses, pigs, and other livestock), as well as wild animals (e.g., animals housed in zoos) to treat or prevent cancer or a precancerous conditions, or to treat or prevent inflammation or otherwise modulate an animal's immune response, are examples of contemplated applications. Exemplary compositions for veterinary use may contain, in addition cis-gnetin H, trans-gnetin H, and/or derivatives thereof as described herein, routine vaccine components such as those included in vaccinations for distemper, rabies, feline leukemia, and other animal diseases, as well as other medications, thereby allowing cis-gnetin H, trans-gnetin H, and/or derivatives thereof to be co-administered with substances that might otherwise trigger inflammation, particularly in sensitive, diseased or vulnerable animals, such as the very young or very old.

Kits

The invention further includes a kit that contains at least one of cis-gnetin H, trans-gnetin H, and/or a derivative thereof, together with instructions for use. In some embodiments, the instructions for use provide instructions for use in the treatment or prevention of cancer, a precancerous condition, a tumor, inflammation, or an inflammatory and/or autoimmune disease disorder or condition. Optionally, the kit includes a pharmaceutically acceptable carrier. The carrier may be separately provided, or it may be present in a composition that includes cis-gnetin H, trans-gnetin H, and/or a derivative thereof. Optionally, the kit may further include one or more additional active agents which can be co-administered with the cis-gnetin H, trans-gnetin H, and/or derivatives thereof. The one or more active agents may have cumulative or complementary activities, as described in more detail elsewhere herein.

Nutritional Supplement and Food Additive cis-gnetin H and/or trans-gnetin H, and/or derivatives thereof, can be packaged as a nutritional, health or dietary supplement (e.g., in pill or capsule form). Additionally, cis-gnetin H and/or trans-gnetin H, and/or derivatives thereof, can be added to a food product to yield what is commonly referred to as a "nutraceutical" food or "functional" food. Foods to which cis-gnetin H and trans-gnetin H can be added include, without limitation, cereals, soups and beverages. In one embodiment, cis-gnetin H, trans-gnetin H, and/or a derivative thereof is formulated as a nutritional supplement or food additive for domestic or domesticated animals, such as pets or livestock. Conveniently, cis-gnetin H, trans-gnetin H, and/or a derivative thereof can be incorporated into animal feed such as fodder and kibble.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1. The Resveratrol Oligomers, Cis- and Trans-Gnetin H, from *Paeonia suffruticosa* Seeds Inhibit the Growth of Several Human Cancer Cell Lines

SUMMARY

Two resveratrol oligomers, cis-gnetin H and trans-gnetin H, purified from the seeds of *Paeonia suffruticosa* have superior activity in inhibiting the proliferation of four human cancer cell lines, A549 (lung), BT20 (breast), MCF-7 (breast) and U2OS (osteosarcoma), and promote cell apoptosis, while having a minimal effect on two normal human epithelial cell lines, HPL1A (lung) and HMEC (breast) used as controls. 10 µM cis-gnetin H or trans-gnetin H caused a dramatic reduction in the cell viability of the four cancer cell lines. The two resveratrol oligomers promote apoptosis by releasing mitochondria cytochrome c, activating caspase 3/7 and inhibiting NF-κB activation. Flow cytometry analysis showed that cis-gnetin H or trans-gnetin H arrested the cell cycle of cancer cells at the G0-G1 phase. Moreover, cis-gnetin H suppressed the growth of xenograft lung tumors in mice. Collectively, our findings demonstrate the promise of the natural compounds cis-gnetin H and trans-gnetin H as candidates for cancer chemotherapy. See Gao et al., 2015, J. Ethnopharmacol., 169:24-33.

Introduction

Much attention has been focused on developing or identifying novel resveratrol derivatives as an important approach for enhancing its bioavailability and bio-efficacy. For instance, Lee et al. showed that ging A, a tetramer of resveratrol, had better inhibition efficacy of lung cancer growth than resveratrol in vivo (Carcinogenesis 2006; 27:2059-2069). The mechanism of the anticancer effects of resveratrol and its derivatives involve various complementary molecular pathways in carcinogenesis. Studies have revealed that resveratrol and its derivatives exert their anticancer effects by inducing apoptosis either through the receptor-mediated pathway or the mitochondria pathway, suppressing NF-κB (nuclear factor kappa B), AP-1 (activator protein 1), Egr-1 (early growth response 1), MAPK (mitogen-activated protein kinases), PKC (protein kinase C), NO/NOS, cell cycle proteins, adhesion molecules, androgen receptors or inflammatory cytokine expression (Aggarwal et al. Anticancer Res., 2004; 24:2783-2840).

*Paeonia suffruticosa* Andrews (PSE) is a well-known Chinese medicine that has been widely used as an anti-tumor, anti-oxidative and anti-inflammatory agent. cis- and trans-gnetin H are two resveratrol oligomers isolated from the seeds of PSE. Although resveratrol is widely considered to be one of the most valuable natural chemopreventive agents and there are numerous studies on the antitumor activities of resveratrol, little is known about the antitumor properties of cis- and trans-gnetin H.

The cis isomer of gnetin H, cis-gnetin H, is a recently discovered novel oligostilbene obtained from the seeds of *Paeonia suffruticosa*. He et al. showed that gnetin H exists as a cis isomer and a trans isomer (Chem. Pharm. Bull. 2010; 58:843-847). Previous studies concerning gnetin H did not identify cis- and trans-forms of the compound; in retrospect, however, it is apparent that these studies utilized the trans form, which was simply referred to as "gnetin H." He et al. (Chem. Pharm. Bull. 2010; 58:843-847) refer to the trans form as "gnetin H" and the cis form as "cis-gnetin H." The earlier publications report investigations of the ability of gnetin H (the trans form) to inhibit the growth of various tumor cell lines (Kim et al., Arch. Pharm. Res. 2002; 25:293-299; Kang et al., Exp. Mol. Med. 2003; 35:467-474; Ha et al., Arch. Pharm. Res. 2009; 32:177-83), but no animal studies were conducted.

The purpose of this study was to investigate the biological role of cis-gnetin H and trans-gnetin H and explore their underlying mechanism of action. We showed that cis-gnetin H and trans-gnetin H can significantly inhibit the growth of a number of tumor cells and that they are capable of promoting apoptosis of cancer cells by releasing mitochondria cytochrome c, activating caspase 3/7, suppressing NF-κB activation, as well as affecting the cell cycle. Collectively our findings suggest that the natural compounds cis-gnetin H and trans-gnetin H have potential as cancer chemotherapy agents.

Materials and Methods

Plant Material.

The seeds of *P. suffruticosa* were collected in Tongling, Anhui province, P. R. China, and identified in September 2012. A voucher specimen (2012001) has been deposited in the Seed Resource Bank of the Institute of Medicinal Plant Development, Chinese Academy of Medical Sciences and Peking Union Medical College.

Extraction and Isolation.

cis- and trans-gnetin H were extracted and isolated from the dried seeds of *P. suffruticosa* (1.2 kg) as described previously (He et al., Chem. Pharm. Bull. 2010; 58:843-847). Compounds were re-suspended in dimethyl sulfoxide (DMSO) (Sigma) to yield the desired concentration and stored at 4° C.

Stability and Conversion of Cis-Gnetin H and Trans-Gnetin H.

For stability testing, cis- and trans-gnetin H were dissolved with methanol to a concentration of 1 mg/ml. The stock solutions were sealed in a glass bottle and kept in the dark at room temperature for 6 months and then the purity of the two compounds was tested using the HPLC method previously described (He et al., J. Liq. Chromatog. Rel. Technol. 2013; 36:1708-1724). For conversion testing, cis- and trans-gnetin H were individually illuminated with a 12-watt fluorescent lamp for 2, 4 and 6 hours, and the compounds were identified using HPLC.

Cell Culture.

The cancer cell lines used in this study included human lung carcinoma (A549), human breast carcinoma (BT20 and MCF-7) and human osteosarcoma (U2OS), with the normal cell lines human peripheral lung epithelial cells (HPL1A) and human mammary epithelial cells (HMEC) serving as controls. A549, BT20, MCF-7, U2OS and HMEC cells were purchased from American Type Culture Collection (ATCC, USA), and HPL1A cells were obtained from Nagoya University, Japan. A549 and BT20 were grown in RPMI-1640 (Sigma), MCF-7 was grown in Dulbecco's Modified Eagle Medium (DMEM) (Sigma) supplemented with 0.01 mg/ml human recombinant insulin (Sigma), U2OS and HMEC were grown in McCoy's 5A (ATCC), and HPL1A was grown in DMEM/F-12K (Sigma). The mediums were supplemented with 10% Fetal Bovine Serum (FBS) (Gibco), 1% penicillin and streptomycin and incubated in a humidified atmosphere with 5% $CO_2$ at 37° C.

Inhibition Assay of Cell Proliferation and IC50 Determination.

The proliferation inhibition potential of cis- and trans-gnetin H was determined by a fluorescence dye staining method. Cells were seeded in a 96-well tissue culture-treated plate (BD Falcon) at a density of 4000 cells/well, and treated with cis- or trans-gnetin H for 48 hours. AlamarBlue dye (Invitrogen) was used to assess the viability of cells according to the manufacturer's instructions; the fluorescent intensity was read on a SpectraMax M2e microplate reader (Molecular Devices Inc.).

For the determination of $IC_{50}$ values, cells were treated with a serial dilution (320 µM, 100 µM, 32 µM, 10 µM, 3.2 µM, and 0.32 µM) of cis- or trans-gnetin H for 48 hours. Cell viability was determined with AlamarBlue dye (Invitrogen) and the $IC_{50}$ values were calculated using non-linear regression analysis.

Multi-Parameter Cytotoxicity Measurement Using an Arrayscan VTI HCS Reader.

A549 cells were seeded in a 96-well plate (BD Falcon) at a density of 4000 cells/well, and then treated with different concentrations (An et al., Mol. Cancer Ther. 2007; 6:61-9; Wilhelm et al., Cancer Res. 2004; 64(19):7099-7109; 100 µM) of cis- or trans-gnetin H for 24 hours and 48 hours. Non-treated cells and cells treated with 100 µM Valinomycin were used as negative and positive controls. After treatment, the cells were stained with a mixture of fluorescent dyes including Hoechst 33342 (blue florescence), cell permeability dye (green florescence) and mitochondrial membrane potential dye (red florescence) (Thermo Scientific). The three dyes allow changes in nuclear morphology, cell membrane permeability and mitochondrial trans-membrane potential to be determined. The cells were fixed and washed, and images for each fluoroprobe were acquired at different channels using suitable filters with a 20× objective and analyzed on the Arrayscan VTI HCS Reader (Thermo Scientific). The Cell Health Profiling BioApplication software (Thermo Scientific) was used for image acquisition and analysis. For each well, at least 400 cells were automatically acquired and analyzed. The average fluorescent intensity was used to quantify changes in each channel and each experiment was performed in triplicate.

Apoptosis Assay by Flow Cytometry.

A549 and BT20 cells were seeded in a 96-well plate (BD Falcon) at a density of 8000 cells/well, and treated with cis- or trans-gnetin H for 24 hours. Apoptosis was assessed using Annexin V/7-AAD double staining as described (Bai et al., Cancer Sci. 2010; 101(2):488-493). Cells were analyzed on a Guava Flow Cytometer (Millipore) using InCyte software and the data was exported to FlowJo software for image display.

Analysis of Cytochrome c by Flow Cytometry.

A549 and BT20 cells were seeded in a 96-well plate (BD Falcon) at a density of 8000 cells/well and treated with 100 µM of cis- or trans-gnetin H for 24 hours. The expression of cytochrome c was evaluated using the FlowCellect Cytochrome c Kit (Millipore) according to the manufacturer's instructions. Cells were stained with either Anti-IgG1-FITC Isotype control or Anti-Cytochrome c-FITC, and data was acquired and analyzed using the Guava Flow Cytometer (Millipore).

Caspase 3/7 Activation Assay.

Caspase 3/7 activity was analyzed using an in-situ luminescent marker. A549 and BT20 cells were seeded in a white 96-well plate (Greiner) at a density of 8000 cells/well, and treated with 100 µM cis- or trans-gnetin H for 24 hours. Caspase activity was then determined using the Caspase-Glo 3/7 Assay (Promega) according to the manufacturer's instructions. The luminescence of each sample was measured using a SpectraMax M2e Microplate Reader (Molecular Devices Inc.).

Cell Cycle Analysis by Flow Cytometry.

A549 and BT20 cells were first synchronized in the G0 phase by culturing cells for 24 hours in serum-free medium and then treated with 100 µM cis- or trans-gnetin H for 24 hours, respectively. Cell cycle analysis was done using propidium iodide (PI) staining as described (An et al., Mol. Cancer Ther. 2007; 6:61-9) and the cells were analyzed on a Guava Flow Cytometer with InCyte software (Millipore).

Inhibition Assay of TNF-α Activated NFκB Translocation Using an Arrayscan VTI HCS Reader.

A549 cells were seeded in 96 well plates (BD Falcon) at a density of 4000 cells/well, and were treated with 100 µM cis- or trans-gnetin H for 2 hrs, followed by treatment of 10 ng/ml tumor necrosis factor-alpha (TNF-α) (Sigma). Untreated cells and cells treated with only 10 ng/ml TNF-α served as controls. Cells were fixed, permeabilized, and stained with Nuclear factor kappa B (NF-κB) primary antibody, Dylight 488 conjugated secondary antibody, and Hoechst 33342 dye, sequentially. The Hoechst and DyLight fluorophores respectively detect changes in nuclear morphology (blue fluorescence) and NF-κB distribution (green fluorescence). Images were acquired at different channels using suitable filters with a 20× objective and analyzed on the Arrayscan VTI HCS Reader (Thermo Scientific). The Nuclear Translocation BioApplication software (Thermo Scientific) was used for image acquisition and analysis. For each well, at least 400 cells were automatically acquired and analyzed. The translocation index was calculated by measuring the average intensity difference of NF-κB between the identified cytoplasmic region and nuclear region (MEAN_CircRingAvgIntenDiffCh2). Experiments were performed in triplicates.

Xenograft Studies.

14 male nude mice (6 weeks old) were injected subcutaneously on both flanks with $2 \times 10^6$ A549 cells. They were injected three times weekly for 4 weeks when tumor volumes reached 200-250 mm³ and then they were treated with 2.4 mg/kg cis-gnetin H in 200 µl 1×phosphate buffered saline (PBS) (n=5), 1 µg/kg staurosporine in 200 µl 1×PBS (n=4) or only 200 µl 1×PBS (n=4) for 4 weeks, 3 times per week. Tumor sizes were measured 3 times per week, and volumes were calculated using the formula [length (mm)]× [width (mm)]²/2 (Warburton et al., Clin. Cancer Res. 2004; 10(7): 2512-2524).

Results

Stability and Conversion of Cis-Gnetin H and Trans-Gnetin H

We first evaluated the convertibility of cis- and trans-gnetin H. Under photo oxidant conditions, trans-gnetin H and cis-gnetin H were observed to be photochemically transformed (FIG. 1C). cis- and trans-gnetin H were extracted with the purities of 93.5% and 92.6%, respectively. After 6-hour treatment, only a slight decrease of the concentration from 93.5% to 88.9% was observed in cis-gnetin H. On the contrary, a dramatic decrease of the concentration from 92.6% to 6.2% was observed in trans-gnetin H after 6-hour treatment, with a large portion (about 86%) converted to its cis-isomer. However, after 6-month storage in the dark at room temperature, the chemical identities of cis-gnetin H and trans-gnetin H exhibited no obvious changes, suggesting that cis-gnetin H and trans-gnetin H are stable under normal storage conditions.

Inhibitory Effects of Cis-Gnetin H and Trans-Gnetin H on the Proliferation of Lung, Breast and Bone Cancer Cell Lines To investigate the inhibitory effects of cis-gnetin H and trans-gnetin H, we conducted cell cytotoxicity tests. Initially we examined the effects of 10 uM cis-gnetin H or trans-gnetin H on lung cancer A549 cells and breast cancer BT20 cells with normal lung HPL1A cells and normal breast HMEC cells serving as controls. Both cis-gnetin H and trans-gnetin H inhibited the growth of the cancer cells as early as 12 hours and this effect increased over time (FIG. 2A), suggesting a time-dependent inhibitory effect. After 48-hours treatment, cis-gnetin H or trans-gnetin H showed about 99% inhibition of both cancer cells. The severe inhibition was confirmed by microscopic examination, which showed cell blebbing, cell shrinkage, chromatin condensation and formation of apoptotic bodies in the cancer cells as compared with the normal polygonal shapes of the control cells. In contrast, no such obvious inhibitory effects were observed in the normal cell controls (HPL1A and HMEC) (data not shown).

Figure 2:
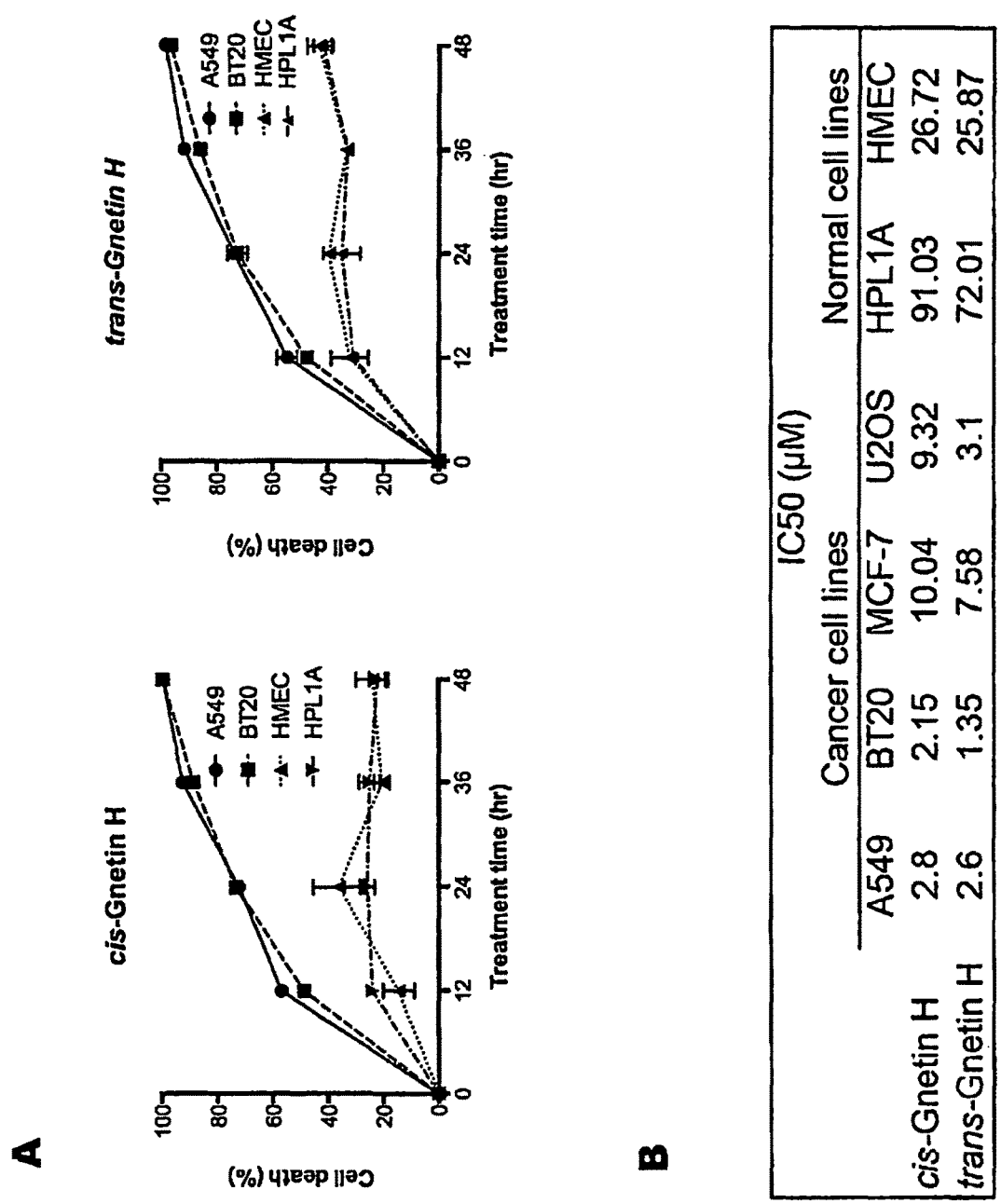
FIG. 2 shows in vitro inhibitory effects of cis-gnetin H and trans-gnetin H on A549 and BT20 cells. A, Inhibitory rates of cis- and trans-gnetin H at a concentration of 10 μM. Inhibitory effects in vitro were assessed in A549, BT20 cells and their normal cell controls after 12, 24, 36 and 48 hours incubation using the AlamarBlue fluorescent assay. B, Values of $IC_{50}$ (μM) of cis- and trans-gnetin H against four malignant cell lines and two normal cell lines in vitro. Serial dilutions of cis- or trans-gnetin H were used to treat the cells for 48 hours and cell viability was assessed using an AlamarBlue fluorescent assay. C, Multiplex cytotoxicity effects of cis- and trans-gnetin H. A549 cells were treated with a serial dilution of cis- or trans-gnetin H, for 24 hrs and 48 hrs, respectively, and the alteration in nuclear size, cell permeability, and mitochondrial trans-membrane potential was simultaneously quantitated by a high-content screening (HCS) reader. 100 μM valinomycin was used as a positive control. Error bars indicate the standard deviations (SDs) from 3 independent experiments. *P<0.05, P<0.01, *P<0.001.
Figure 2:
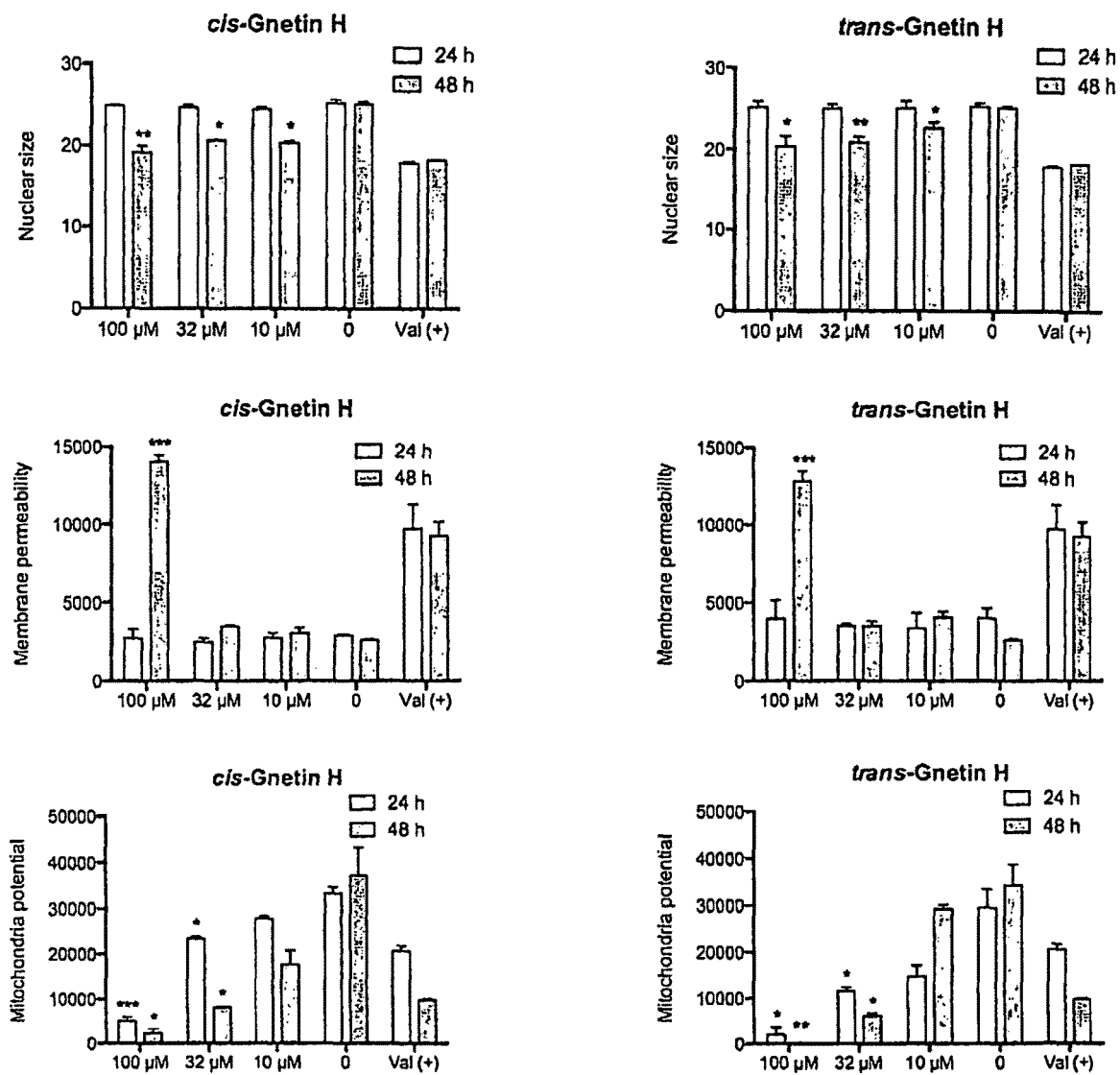
Figure 7:
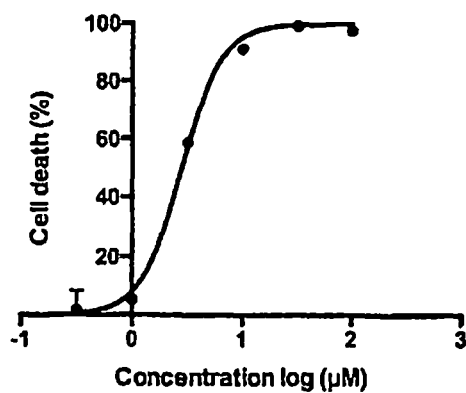
FIG. 7 shows the determination of the $IC_{50}$ (μM) values of cis-gnetin H and trans-gnetin H against cancer and normal cell lines in vitro. A serial dilution of cis- or trans-gnetin H were used to treat four human malignant cell lines, A549, BT20, MCF-7 and U2OS, respectively, for 48 hours and cell viability was assessed using an AlamarBlue fluorescent assay. Two normal human cell lines, HPL1A and HMEC, served as controls. Values are means±SD of 3 independent experiments.
Figure 7:
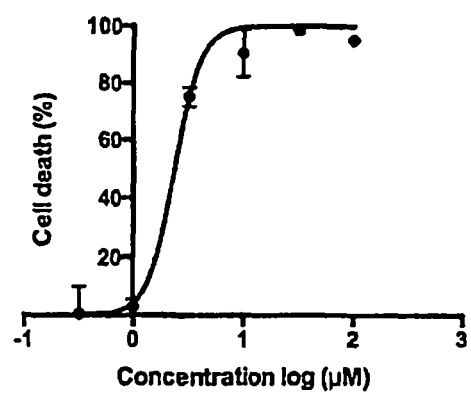
Figure 7:
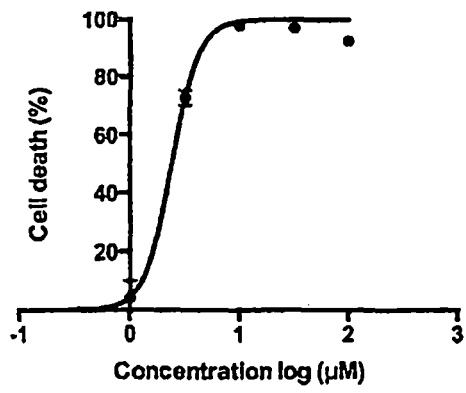
Figure 7:
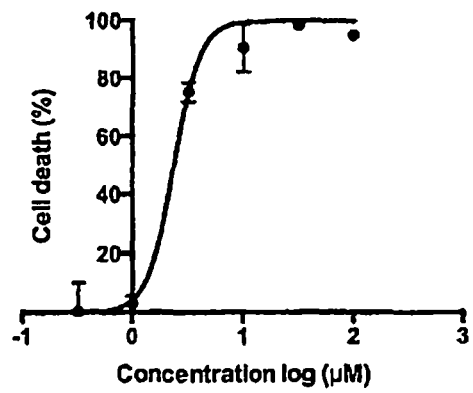
Figure 7:
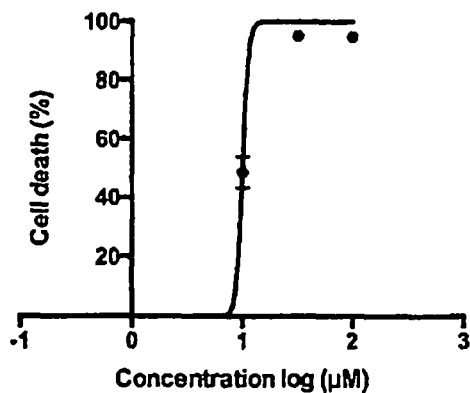
Figure 7:
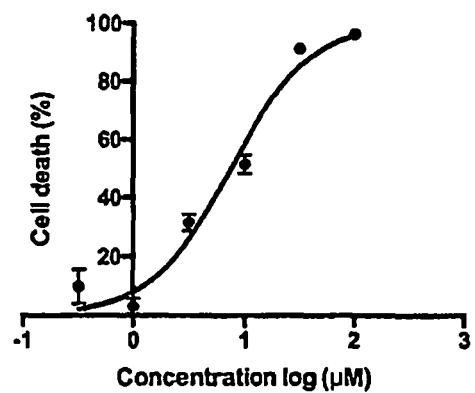
Figure 7:
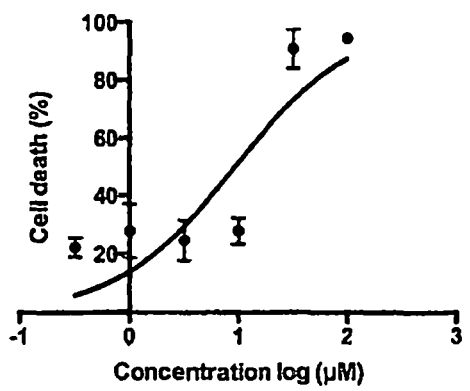
Figure 7:
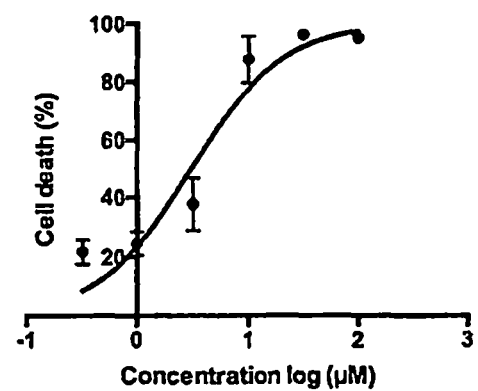

To further evaluate the effective dose of cis-gnetin H and trans-gnetin H, $IC_{50}$ values (FIG. 7) were determined for cis-gnetin H and trans-gnetin H, respectively, using A549 (lung cancer), BT20 (breast cancer), U2OS (osteosarcoma) and MCF-7 (breast) cells, with HPL1A (lung) and HMEC (breast) normal cells serving as controls. Both cis-gnetin H and trans-gnetin H showed dramatic inhibition of the malignant cells, with $IC_{50}$ values ranging from 1.35 µM to 10.04 µM (FIG. 2B). The $IC_{50}$ values in malignant cells were significantly less than those in normal cells (25.87 to 91.03 µM) indicating significantly lower toxicity to normal cells.

Cis-Gnetin H and Trans-Gnetin H Cause Multiplex Cytotoxicity Including Nuclear Condensation, Changes in Cell Permeability and Disruption of the Mitochondrial Transmembrane Potential High-content screening (HCS) image analysis allows simultaneous measurement of the nuclear morphology, plasma membrane permeability and mitochondria potential as indicators of cellular injury. Disruption of the mitochondria potential tends to be an early indicator of cellular injury, whereas nuclear shape changes (nuclear condensation) and an increase in plasma membrane permeability are indicative of acute toxicity (Minamikawa et al., Exp. Cell Res. 1999; 246:26-37; Zakeri et al., The Study of Cell Death by the Use of Cellular and Developmental Models. In When Cells Die. New York: Wiley-Liss. 1998).

Figure 8:
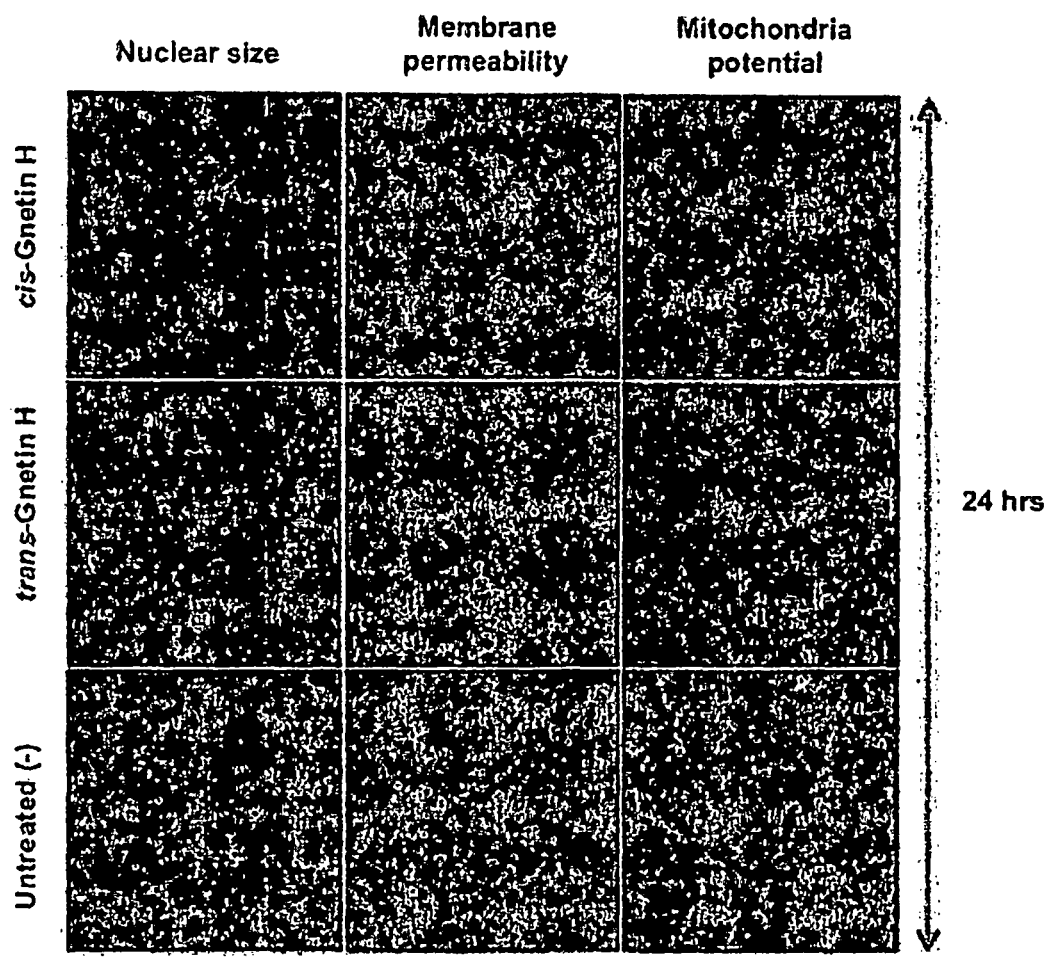
FIG. 8 shows HCS images showing simultaneous monitoring of changes in nuclear size, cell permeability, and mitochondrial trans-membrane potential. A549 cells were treated with 100 μM cis- or trans-gnetin H, for 24 hrs (A) and 48 hrs (B), respectively, or were treated with 100 μM valinomycin as a positive control.
Figure 8:
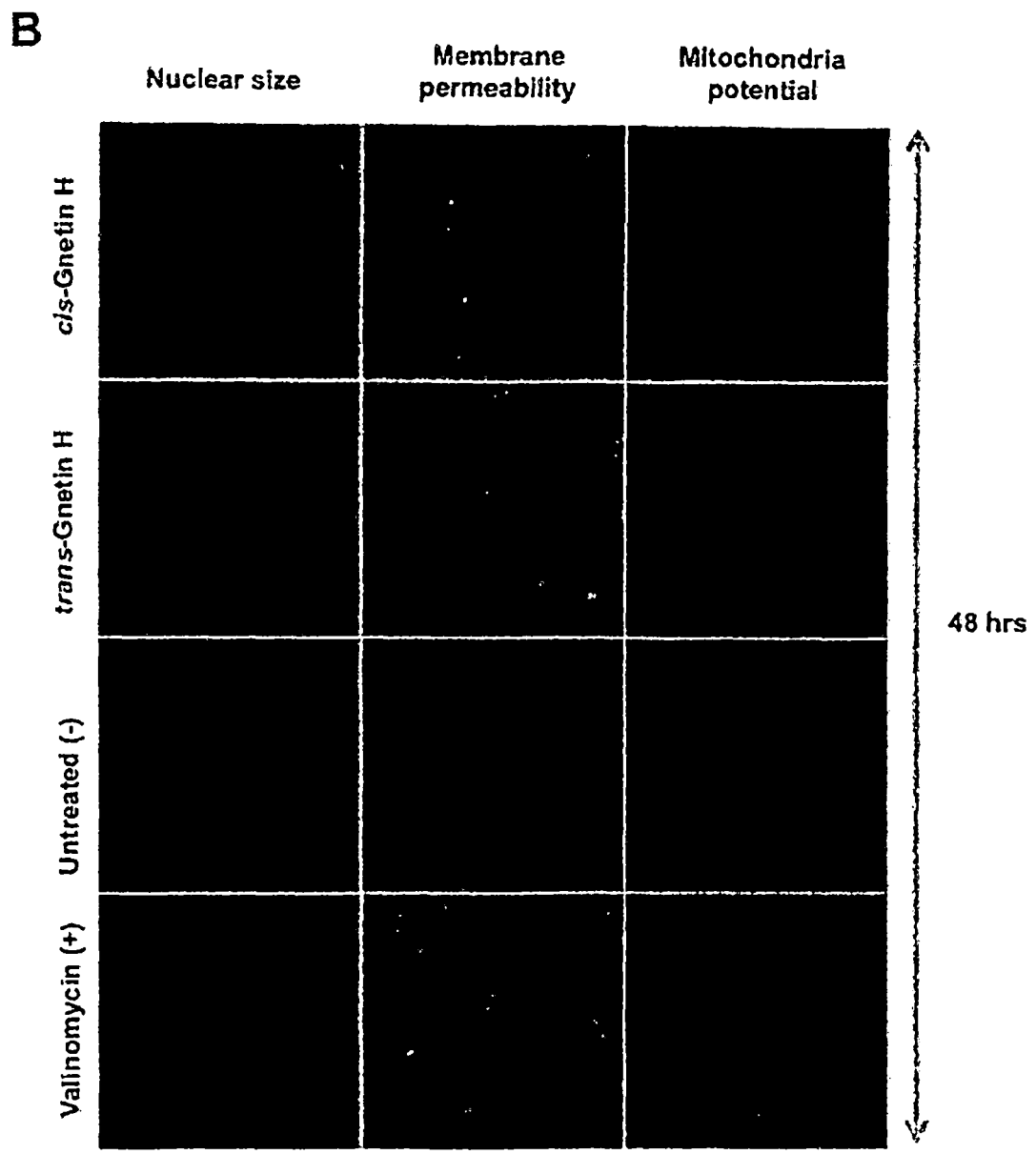

To further study the inhibitory effects of cis-gnetin H and trans-gnetin H, treated A549 cells were examined for cellular changes using HCS analysis. Untreated A549 cells displayed normal nuclear size, intact plasma membrane integrity and brightly labeled mitochondria. However, after 24 hours treatment with cis-gnetin H or trans-gnetin H, A549 cells showed decreased mitochondria potential as evidenced by lower red florescent intensity, but no alternation of nuclear size and plasma membrane permeability, suggesting that they suffered from early or moderate cellular injury. After treatment for 48 hours, the cells exhibited nuclear condensation, increased plasma membrane permeability as evidenced by higher green florescent intensity, and loss of mitochondrial potential, suggesting that they were undergoing late or severe cellular injury (FIG. 8). As shown in FIG. 2C no alternation in nuclear size occurred following 24 hrs treatment by cis-gnetin H or trans-gnetin H, but a reduction in nuclear size did occur after 48 hrs. Similarly, no alternation in cell permeability occurred following 24 hrs treatment by cis-gnetin H or trans-gnetin H, but an increase in cell permeability was observed after 48 hrs. In comparison, a reduction in the mitochondria transmembrane potential occurred after both 24 hrs and 48 hrs of treatment. In addition, the cytotoxicity effects of cis-gnetin H and trans-gnetin H occurred in a dose-dependent manner as quantified in FIG. 2C.

Figure 3:
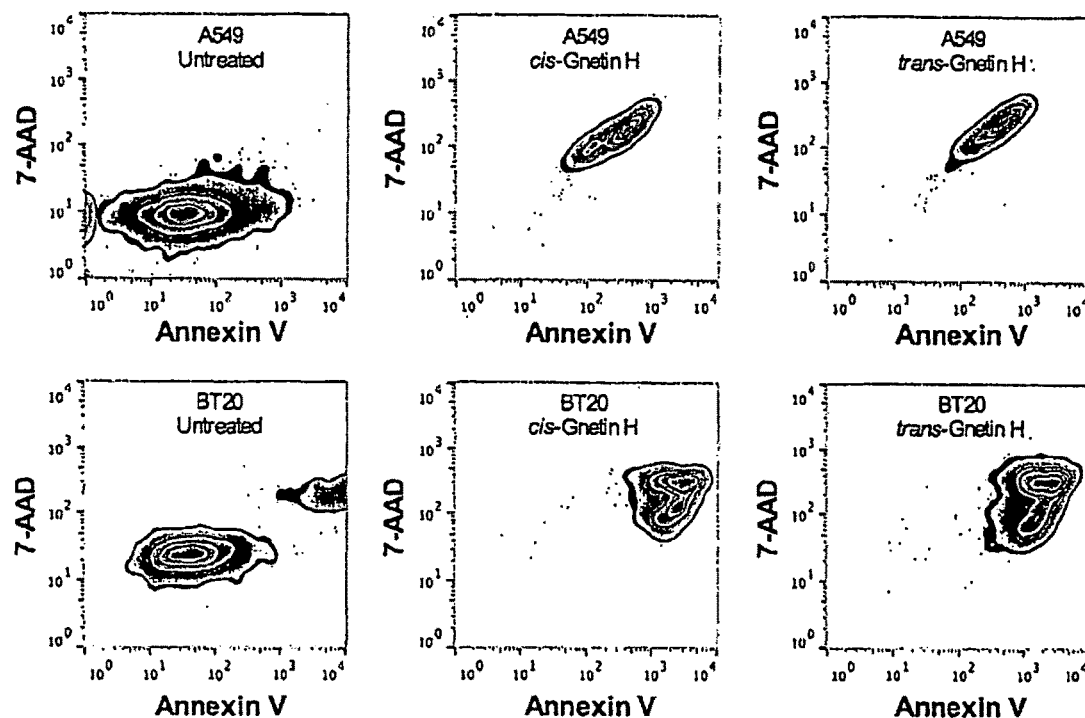
FIG. 3 shows evaluation of apoptosis induced by cis-gnetin H or trans-gnetin H in A549 and BT20 cells. A, Flow cytometry analysis of apoptosis induced by cis- or trans-gnetin H in A549 and BT20 cells. B, Apoptosis rates for A549 and BT20 cells treated with different concentrations of cis- or trans-gnetin H. A549 and BT20 cells were treated with different concentrations of cis- or trans-gnetin H for 24 hours, and assayed using Annexin V/7-AAD double staining. C, Cytochrome c release in A549 and BT20 cells induced by cis- or trans-gnetin H. Blue curve shows the isotype control, red curve peak shows the negative control (untreated cells), and the yellow curve shows the tested samples. The numbers on the upper corners show the percentage of cells that released or did not release cytochrome c. A549 and BT20 cells were treated with 100 μM cis- or trans-gnetin H for 24 hours, and the release of cytochrome c was assessed using Anti-Cytochrome c-FITC staining. D, Caspase 3/7 activation in A549 cells treated with cis- or trans-gnetin H. A549 cells were treated with 100 μM cis- or trans-gnetin H for 4 hours and assessed using Caspase-Glow 3/7 assay. 1 μM staurosporine served as the positive control and untreated cells were used as the negative control. Error bars indicate the SDs from 3 experiments. *P<0.05, **P<0.01.
Figure 3:
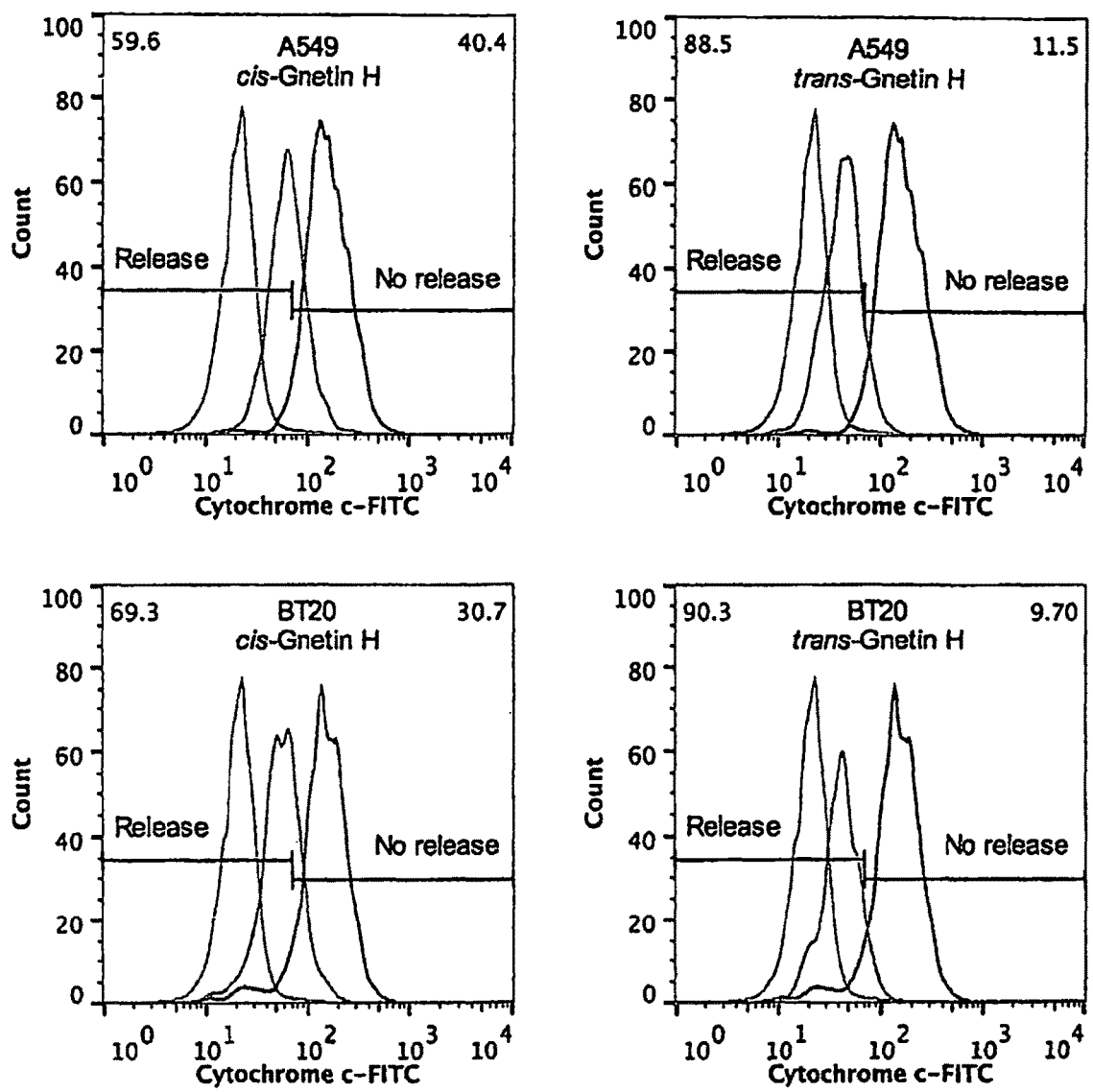
Figure 3:
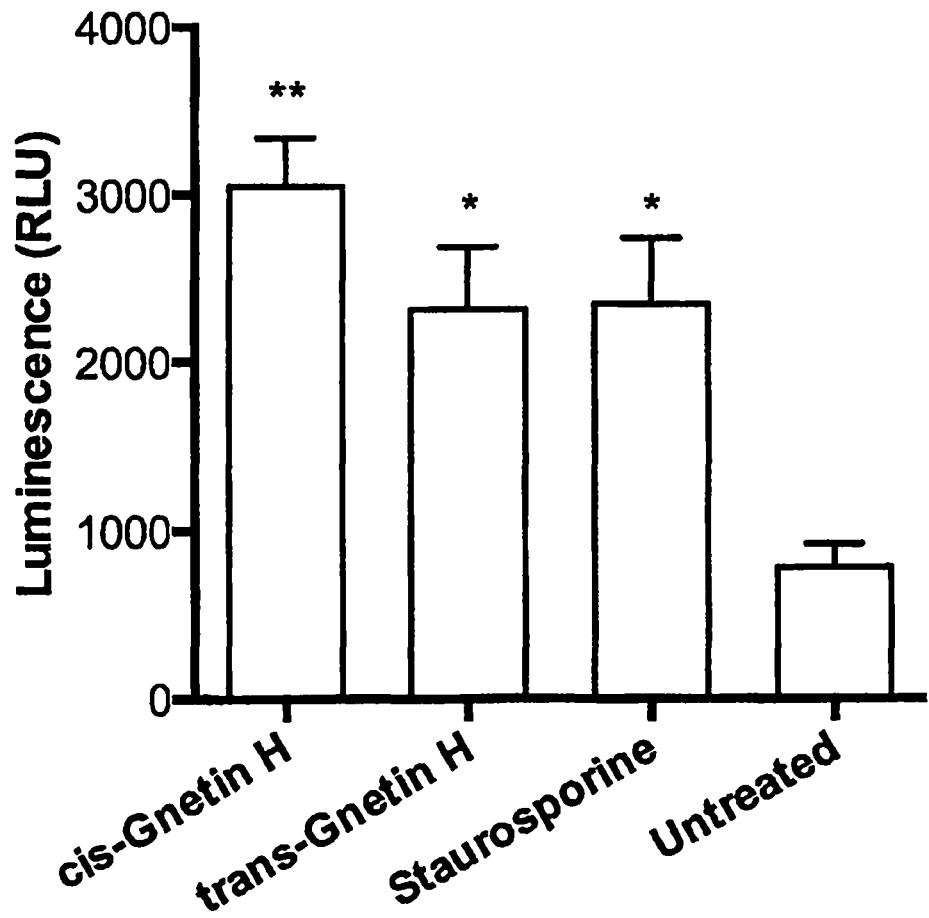

Cis-Gnetin H and Trans-Gnetin H Promote Apoptosis, Cytochrome c Release and the Activation of Caspases 3/7 in Cancer Cells To determine how cis-gnetin H and trans-gnetin H caused the death of cancer cells, we employed the Annexin V/PI double staining assay using the two cell lines that were the most sensitive to cis-gnetin H and trans-gnetin H, A549 and BT20, and observed that cis-gnetin H or trans-gnetin H could induce apoptosis in A549 and BT20 cells at a dose of 100 µM (FIG. 3A). Moreover, we observed that the test compounds induced apoptosis in a dose-dependent manner (FIG. 3B).

Cytochrome c is a key mitochondrial protein and the release of mitochondrial cytochrome c is an important hallmark in the pathway of apoptosis and is considered to be a point of no return in the apoptotic process (Newmeyer et al., Cell 2003; 112:481-490). For this reason, we assessed the loss of mitochondrial cytochrome c in A549 and BT20 cells. All treated cells showed a downward shift in fluorescence when compared with the untreated control (FIG. 3C), suggesting that cytochrome c is released from mitochondria to the cytoplasm in the treated cells.

Caspase-3 and -7 are early apoptotic markers in mammalian cells (Thornberry et al., Science 1998; 281(5381): 1312-1316). To clarify the pathway of cis-gnetin H- or trans-gnetin H-induced apoptosis, we determined caspase-3 and -7 activities using a luminogenic substrate containing the tetrapeptide sequence that is selective for caspase-3 and -7. As shown in FIG. 3D, in A549 cells treated by cis-gnetin H or trans-gnetin H, activities of caspase 3/7 increased 3.65-fold or 2.7-fold, respectively compared with untreated A549 cells. Staurosporine, a known caspase activator, was used as a positive control. These results suggest that cis- and trans-gnetin H induce apoptosis by promoting the activities of caspase-3 and -7.

Cis-Gnetin H and Trans-Gnetin H Affect the Cell Cycle of Cancer Cells

Figure 4:
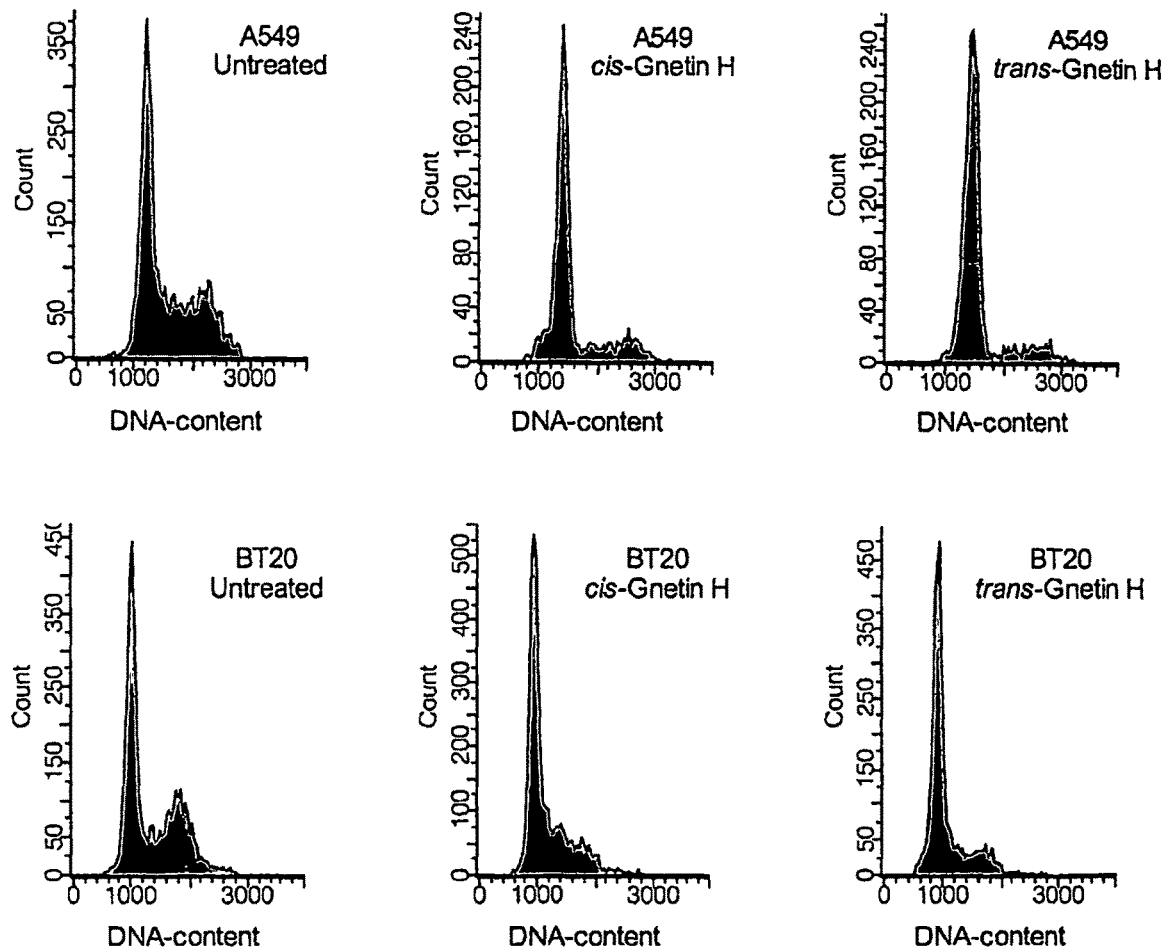
FIG. 4 shows cell cycle distribution of A549 and BT20 cells treated with cis-gnetin H or trans-gnetin H. A, Cell count of the cells in different cell cycle stages. B, Percentage of cell population in different cell cycle stages. A549 cells and BT20 cells were synchronized for 24 hours prior to treatment with 100 μM cis- or trans-gnetin H for 24 hours, and then assessed using PI staining. Error bars indicate SDs from 3 wells.
Figure 4:
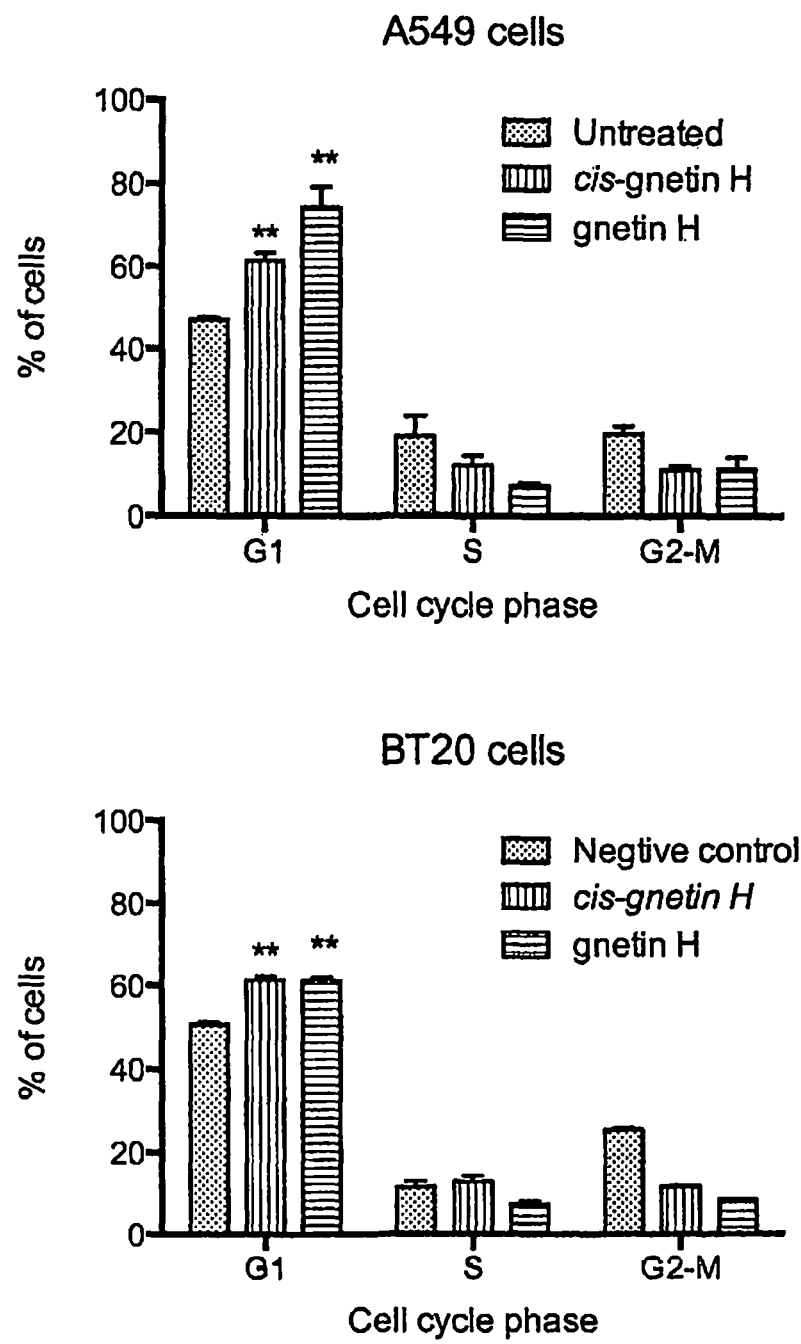

To examine if cis-gnetin H and trans-gnetin H also altered the distribution of the cell cycle, we performed a cell cycle analysis. cis-gnetin H and trans-gnetin H induced a marked increase in the cell number at the G0-G1 phase, with a corresponding decrease in the other phases in both cancer cell lines (FIG. 4A), suggesting that cis-gnetin H and trans-gnetin H disrupt the G1-S transition during cell division. Under treatment with 100 µM of cis-gnetin H or trans-gnetin H, the G0-G1 subpopulation of A549 and BT20 cells increased significantly, while the M and G2-S subpopulation of the cells showed a significant decrease. (FIG. 4B).

Cis-Gnetin H and Trans-Gnetin H Inhibit TNF-α Activated NF-κB Translocation

Figure 5:
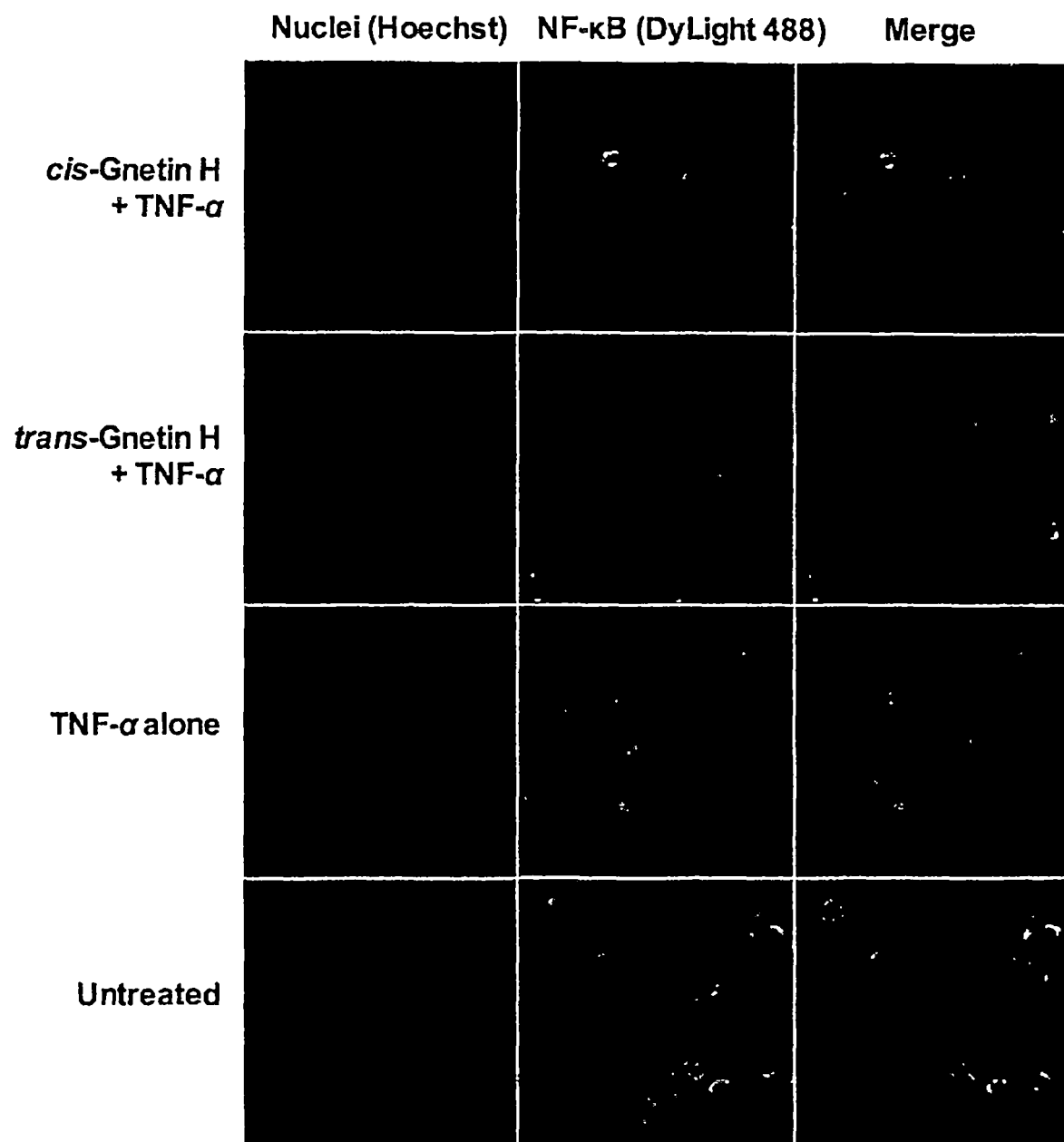
FIG. 5 shows inhibition on TNF-α-induced NF-κB nuclear translocation by cis-gnetin H or trans-gnetin H in A549 cells. A, HCS images of NF-κB translocation. B, Values of NF-κB nuclear translocation in A549 cells after the treatment of cis- or trans-gnetin H. A549 cells were treated with 100 μM of cis- or trans-gnetin H for 2 hours, followed by stimulation with 10 ng/ml TNF-α. Cells treated with TNF-α alone served as the negative control. Error bars indicate SDs from 3 wells. P<0.01, *P<0.005.
Figure 5:
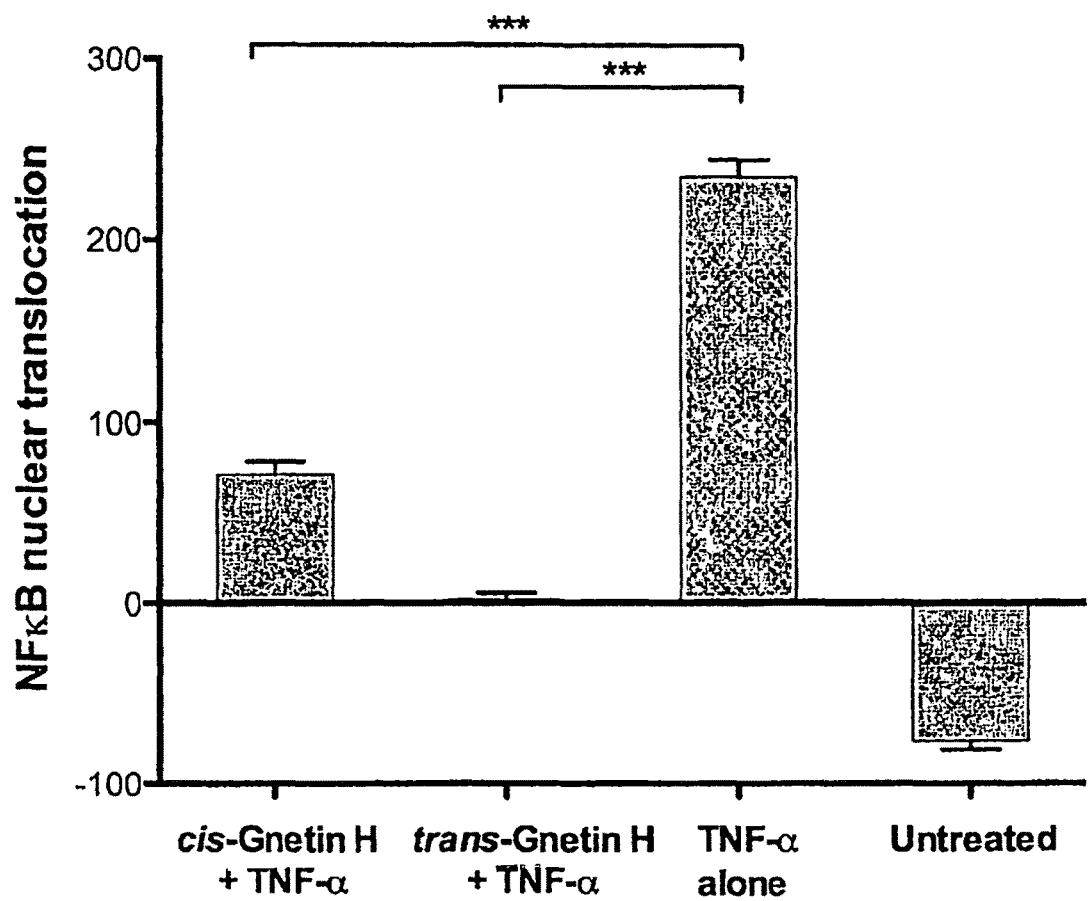

NF-κB is a transcription factor that controls the transcription of anti-apoptotic and cell proliferation genes, and is essential for the survival of cancer cells (Sethi et al., Trends Pharmacol. Sci. 2009; 30:313-321). We thus assessed the ability of cis-gnetin H and trans-gnetin H to inhibit TNF-α induced NF-κB activation in vitro using DyLight 488-conjugated anti-NF-κB antibody. As shown in FIG. 5, in A549 cells treated in normal medium without addition of the compound, a high fluorescent intensity of NF-κB was found in the cytoplasm, but rarely in the nuclei, indicating that NF-κB is not activated under normal conditions. Following stimulation with TNF-α, the NF-κB fluorescent intensity significantly increased in the nuclear region, consistent with NF-κB translocation from the cytoplasm to the nucleus. However, in A549 cells treated with cis-gnetin H or trans-gnetin H, we observed significant inhibition of TNF-α-induced NF-κB nuclear translocation as evidenced by low nuclear NF-κB-related fluorescence intensity.

Cis-Gnetin H Suppresses the Growth of Xenograft Lung Tumors in Mice

Figure 6:
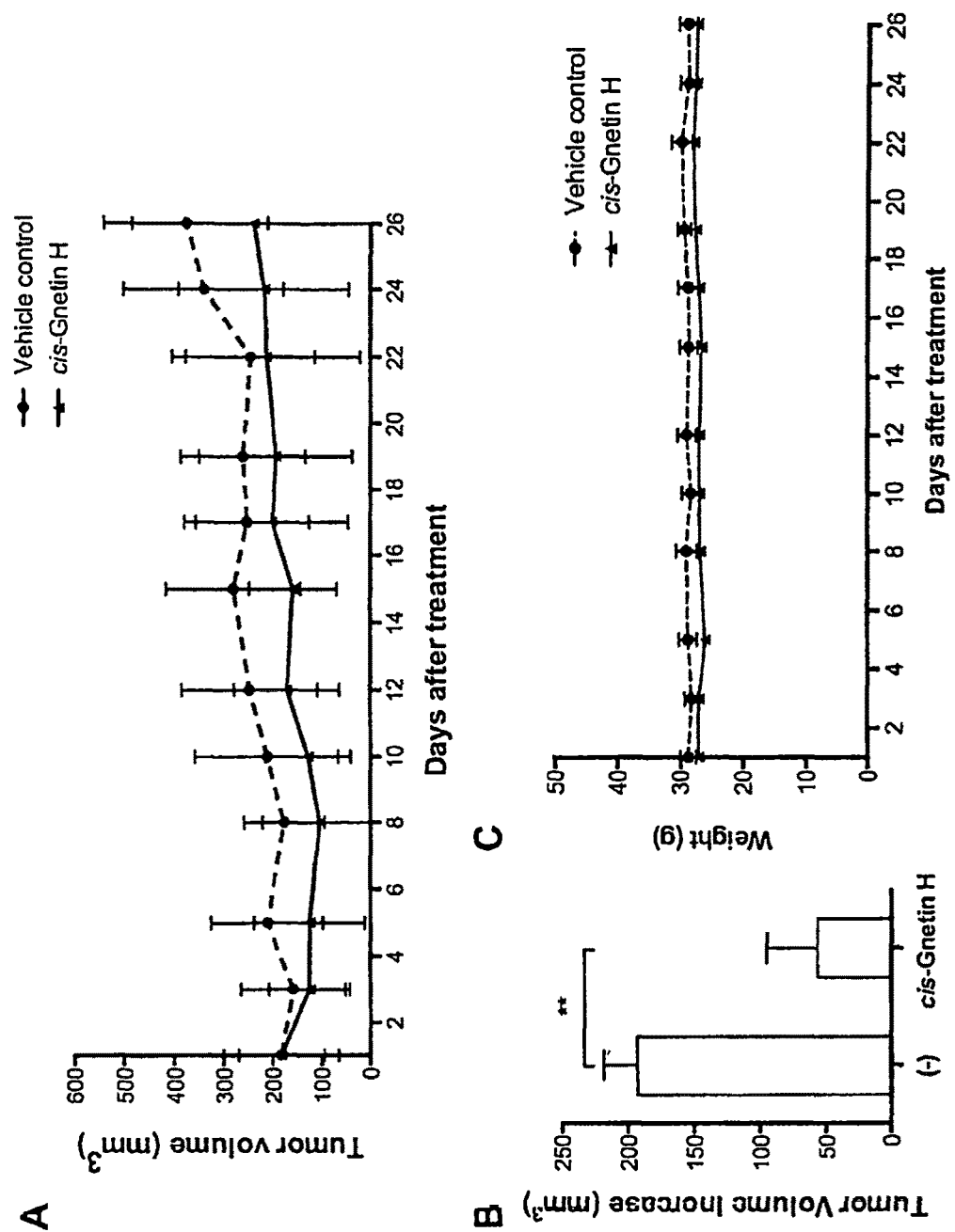
FIG. 6 shows in vivo effects of cis-gnetin H on mouse xenograft lung tumors. A, Tumor size of mouse A549 xenografts. B, Inhibitory effects of cis-gnetin H on xenograft tumor volumes. C, Effects of cis-gnetin H on the weight of nude mice. Four-week old nude mice treated with cis-gnetin or vehicle control every two days for 26 days. Error bars indicate SDs from 5 individual mice. **P<0.01.

Animal models are a key tool for determining the efficacy of potential new therapeutics and thus we wanted to test our compounds using the established lung cancer xenograft mouse model. Since the antitumor activities of cis-gnetin H and trans-gnetin H were very similar in all our in vitro testing that we did and because cis-gnetin H was much more stable than trans-gnetin H and far easier to synthesize in large quantities, we decided to utilize cis-gnetin H in a xenograft mouse model. To test whether cis-gnetin H had anti-tumor activity in vivo, we analyzed the effects of cis-gnetin H on the growth of established A549 lung cancer xenografts. Compared to the control mice which showed a 147 mm$^3$ increase (equals to 65%) in average tumor size, mice treated with cis-gnetin H only had a 89 mm$^3$ (equals to 39%) increase in average tumor size, while the control staurosporine had a 85 mm$^3$ (equals to 37%) increase in average tumor size (FIG. 6A). Interestingly, cis-gnetin H was more effective in reducing the size of large tumors (68% less increase compared to the untreated control) than in reducing the size of small tumors (39% less increase compared to the untreated control). In addition no apparent alteration on food intake or body weight was observed in the treated animals (FIG. 6B), suggesting that cis-gnetin H has in vivo inhibiting activity on lung tumor growth without dramatic toxic side effects.

Discussion

Herbal medicines have been employed in the treatment of cancers in Asia and the Far East for quite some time now, and many of them have been shown to be effective and safe in clinical practice. However, which chemicals in these botanicals represent the active ingredient largely remains unknown and therefore evidence-based studies to determine the bioactive compounds have increased dramatically over the last few years. Peony is a well-known Chinese medicine that has been widely used as an anti-tumor, anti-oxidative and anti-inflammatory agent. Previously we isolated cis-gnetin H, trans-gnetin H, along with other resveratrol oligomers from the seeds of peony (He et al., Chem. Pharm. Bull. 2010; 58:843-847). In this study we report the in vitro bioactivity of cis-gnetin H and trans-gnetin H, the in vivo anti-tumor activity of cis-gnetin H, and elucidate the mechanism of the anti-tumor activity of these two compounds.

Natural oligostilbenes can be converted from the trans configuration to the cis configuration in the presence of $H_2O_2$, metal, UV and acid (Lin et al. Stud. Nat. Prod. Chem. 2006; 33:601-644). Generally the trans isomer of doubly substituted ethylenes is more stable than its cis counterpart because of the more favorable electrostatic and steric interactions of the trans conformer. Nevertheless, a recent study showed that there can be exceptions, and that the cis isomer of some doubly substituted ethylenes possesses unusual stability, a fact that has been referred to as the cis-effect (Zhao et al., Acta Physico-Chimica Sinica 2013; 1: 43-54).

Stilbenes and oligostilbenes, which are doubly substituted ethylenes, should generally be more stable in the trans configuration than their cis counterpart because of the more favorable electrostatic and steric interactions of the trans conformer (Zhao et al., Acta Physico-Chimica Sinica 2013; 1: 43-54; Bingham, J. Am. Chem. Soc. 1976; 98:535-540). Two well-known examples are stilbene (Fischer et al., J. Chem. Soc. B. 1968:1156-1158) and resveratrol (Bonda et al., Cosmetics Toiletries. 2011:126: 652-660). Paradoxically, our study showed that cis-gnetin H is more stable than trans-gnetin H as trans-gnetin H is easily converted to cis-gnetin H by photooxidation. The cis conformer of doubly substituted ethylenes can occasionally be more stable than the trans conformer and this phenomenon has been termed the cis or gauche effect (Zhao et al., Acta Physico-Chimica Sinica 2013; 1: 43-54; Bingham, J. Am. Chem. Soc. 1976; 98:535-540). Two other oligostilbenes that exhibit the cis effect are vitisin A and e-viniferin (Lin et al. Stud. Nat. Prod. Chem. 2006; 33:601-644).

Resveratrol is widely considered to be one of the most valuable natural chemopreventive agents as it possesses significant inhibitory activities to cancer cells while having low or no cytotoxicity to normal cells (Dorrie et al., Cancer Res. 2001; 61(12):4731-4739). Resveratrol has been reported to have $IC_{50}$ values of 8.9 µM (Yin et al. Pacific J Cancer Prev. 2013; 14(3):1703-1706), above 10 µM (Weng et al., J. Agric. Food Chem. 2009; 57:5235-5243), or higher (Liu et al., Mol. Nutr. Food Res. 2010; 54:S196-S204) against the A549 lung cancer cell line. Our results show that cis-gnetin H and trans-gnetin H are more effective in anti-tumor proliferation than resveratrol. A couple of studies have been conducted previously on trans-gnetin H. Kim et al. (Kim et al., Arch. Pharm. Res. 2002; 25:293-299) found trans-gnetin H exhibited marked cytotoxic activity against C6 (mouse glioma), HepG2 (human liver), Hela (human cervix), MCF-7 (human breast) and HT-29 (human colon) cancer cell lines with IC50 values ranging from 12.7 to 61.7 µg/ml. Kang et al. (Kang et al., Exp. Mol. Med. 2003; 35:467-474) demonstrated that trans-gnetin H reduced the viability of HL-60 (human leukemia) cells in a dose-dependent manner with an IC50 value of 25 µM, and that HL-60 cells treated with 25 µM of trans-gnetin H caused an 11% increase of the sub-G1 population. Ha et al. (Arch. Pharm. Res. 2009; 32:177-83) showed that trans-gnetin H inhibited L1210 (mouse leukemia) cells and had an IC50 value of 40.1 µM. We investigated the antiproliferation activity of both cis-gnetin H and trans-gnetin H using a panel of cancer cell lines (A549, BT20, MCF-7 and U2OS) and observed 2-9 fold more antiproliferation activity of trans-gnetin H than has been previously reported (Kim et al., Arch. Pharm. Res. 2002; 25:293-299; Kang et al., Exp. Mol. Med. 2003; 35:467-474; Ha et al., Arch. Pharm. Res. 2009; 32:177-83). We also observed that trans-gnetin H was slightly more inhibitory to cancer cell lines than its cis-isomer. Consistent with our observation, Anisimova et al. (Chem. Cent. J. 2011; 5: 88) reported that trans-resveratrol was more effective as an anticancer agent against prostate cancer compared with cis-resveratrol.

Apoptosis plays a critical role in the efficacy of anticancer agents. Our results showed that cis-gnetin H and trans-gnetin H share a common mechanism for the induction of apoptosis in cancer cells. We observed typical apoptotic phenomena including nucleus condensation and decrease of mitochondria membrane potential using high-content screening, and this conclusion was further supported by the Annexin V apoptosis assay. Apoptotic cell death can be induced through the receptor-mediated or the mitochondria-mediated signaling pathways, and the disruption of mitochondria transmembrane potential and the release of cytochrome c are key events in mitochondria-mediated apoptosis pathways (Li-Weber, Cancer Lett. 2010; 332(2): 304-312). In this study we demonstrated that cis-gnetin H and trans-gnetin H triggered the mitochondrial apoptotic pathway in tumor cell lines as evidenced by the release of mitochondrial cytochrome c and the activation of the downstream effectors caspase 3/7.

NF-κB is closely associated with cancers and acts through the transcription of anti-apoptotic proteins, which causes increased proliferation of cells and tumor growth (Pikarsky et al., Nature 2004; 431:461-6; Escarcega et al., Clin. Oncol. 2007; 19:2154-161). Therefore, targeting the NF-κB signaling pathway represents an attractive therapeutic option for cancer treatment protocols. Resveratrol can suppress proliferation and induce apoptosis of various cancer cells by regulating nuclear factor NF-κB activities (Sun et al., Cancer Genet. Cytogenet. 2006; 165:9-19). In this study, we demonstrated that the treatment of A549 cells with cis-gnetin H or trans-gnetin H resulted in a strong inhibition of cytokine-induced NF-κB activation, suggesting that cis-gnetin H and trans-gnetin H act as NF-κB inhibitors as well and may induce apoptosis mediated by the inhibition of the NF-κB signaling pathway, which contributes to the pro-apoptotic action of cis-gnetin H and trans-gnetin H in cancer cells.

Proliferation arrest is another main effect that is caused by resveratrol on a variety of cancer cells, and it has been suggested that many stilbene compounds cause a block of cells in a specific phase of the cell cycle, acting as phase-specific drugs (Sun et al., Cancer Genet. Cytogenet. 2006; 165:9-19; Benitez et al., J. Androlog. 2007; 28(2):282-293; Horvath et al., Anticancer Res. 2007; 27(5A): 3459-3464). In this study we examined the phase-specific effect of cis-gnetin H and trans-gnetin H on cell proliferation in both lung and breast cancer cells and showed that both compounds arrested the cell cycle of the cancer cells at the G0-G1 phase. It remains to be determined how the key proteins, Cyclin Dl, CDK4, p21, p53, etc. (Harper et al., Cell 1993; 75:805-816; Kohn et al., Mol. Biol. Cell. 1999; 10:2703-2734) involved in regulating the cell cycle, are impacted by cis-gnetin H and trans-gnetin H.

Finally, we demonstrated that cis-gnetin H significantly suppressed the growth of xenograft tumors in a mouse model. Interestingly, cis-gnetin H was more effective in reducing the size of large tumors than in reducing the size of small tumors, suggesting it might work by suppressing the regulators for fast-growing tumors, such as the vascular endothelial growth factor (VEGF)-dependent Raf/MEK/ERK pathway that is involved in tumor angiogenesis and metastasis (Wilhelm et al., Cancer Res. 2004; 64(19):7099-7109).

In conclusion, we show that both cis-gnetin H and trans-gnetin H have in vitro activity specifically in suppressing the proliferation of a number of tumor cell lines, that their inhibitory effect is caused by triggering apoptosis, and that cis-gnetin H has in vivo activity against anti-lung cancer cells. Collectively, our studies strongly suggest that cis-gnetin H and trans-gnetin H can be novel, efficient and safe chemotherapeutic agents for the treatment of a number of cancers.

Example 2. Crude Extract from *Paeonia suffruticosa* Containing Cis- and Trans-Gnetin H The dried seeds of *P. suffruticosa* (4.0 kg) were pulverized and extracted successively with 90% ethanol (EtOH) (4×6L) and 70% EtOH (2×6L) by soaking at room temperature for 24 h each time. The combined EtOH extracts were concentrated under reduced pressure at 60° C. to afford a dark-brown residue (840 g). The residue was resuspended at 10 mg/mL in DMSO and then used directly in the bioassay.

Table 1 shows that the extract prepared from *Paeonia suffruticosa* seeds that is used to purify cis-gnetin H and trans-gnetin H has inhibitory activity against multiple cancer cells.

TABLE 1

IC50 of the crude extract from *Paeonia suffruticosa* seeds used to purify cis-gnetin H and trans-gnetin H.

| IC50 | Cancer cell lines | | | | Normal cell lines | |
|---|---|---|---|---|---|---|
| | A549 | BT20 | MCF-7 | U2OS | HPL1A | HMEC |
| cis-gnetin H | 2.8 μM | 2.15 μM | 10.04 μM | 9.32 μM | 91.03 μM | 26.72 μM |
| trans-gnetin H | 2.6 μM | 1.35 μM | 7.58 μM | 3.1 μM | 72.01 μM | 25.87 μM |
| crude extract | 11.8 μg/ml | 4.22 μg/ml | 8.27 μg/ml | ND | 81.42 μg/ml | 47.69 μg/ml |

ND = not determined

Example 3. Cis- and Trans-Gnetin H Isolated from *Paeonia suffruticosa* Exert Anti-Inflammatory Effects in Human THP-1 Cells by Suppressing Phosphorylation of the Inhibitor Kappa B Kinase Summary The inflammatory response is an important mechanism in host defense; however, overstimulation and chronic induction of the inflammation is involved in many important human diseases. Currently, tumor necrosis factor-alpha blockers such as infliximab and adalimumab along with methotrexate are used in severe and chronic inflammation. However, there are severe side effects and limitations associated with current treatments. cis- and trans-gnetin H are compounds isolated from the seeds of *Paeonia suffruticosa*, a medicinal plant used in traditional Chinese medicine for various treatments that include inflammatory diseases. We investigated possible anti-inflammatory mechanisms of these compounds against LPS-stimulated human THP-1 cells for their anti-inflammatory effects. Phorbol 12-myristate 13-acetate (PMA)-differentiated THP-1 cells were pretreated with various concentrations of the cis- and trans-gnetin H with and without lipopolysaccharide (LPS). Following treatment, cytotoxicity and the cytokine responses of TNF-α, IL-1β, and IL-8, were measured. We also characterized the nuclear translocation of NF-κB subunit, p65 (RelA), by immunofluorescence and then investigated NF-κB activation by measuring the phosphorylation of NF-κB mediators by western blot. We found that cis- and trans-gnetin H significantly inhibited the cytokine responses in a concentration-dependent manner without affecting cell viability. cis- and trans-gnetin H also effectively inhibited the nuclear translocation of p65 and inhibited the phosphorylation of IKK-β, IκB α, as well as p65. While both compounds showed promising anti-inflammatory effects, trans-gnetin H was determined to be more effective in suppressing cytokine responses. In conclusion, we demonstrated cis- and trans-gnetin H exert anti-inflammatory effects by suppressing the key signaling molecule involved in the NF-κB pathway and suggest potential therapeutic usage for conditions and diseases associated with chronic inflammation.

Introduction

Inflammation is central to many disease processes including, for example, autoimmune diseases and chronic inflammatory diseases, and there are relatively few classes of compounds used as anti-inflammatory drugs, with steroids and nonsteroidal anti-inflammatory drugs (NSAIDS) comprising the major classes. Recently, monoclonal antibodies and fusion proteins have been developed to treat chronic inflammation (Thalayasingam et al., Best Pract. Res. Clin. Rheumatol., 2011, 25:549-67), however, these treatments can cause severe side effects such as allergic reactions, increased risk of infections, malignancies, and risk of stroke, and are thus their use has been limited to severe inflammatory diseases such as rheumatoid arthritis and ankylosing spondylitis (Bezalel et al., 2012, Isr. Med. Assoc. J., 14:508-14; Bjarnason et al., 1993, Gastroenterology, 104:1832-47; Bongartz et al., 2006, JAMA, 295: 2275-2285; Diamantopoulos, 2013, Int. Cardiol. 167:1719-1723). Another reason for the interest in new anti-inflammatory therapeutics is the associated cost of inflammatory conditions well exceeds the costs associated with cancer treatment. Almost every pathogenic process possesses an inflammatory component and the current classes of inflammatory drugs all have substantial side effects, contraindicating their use.

Recently, more attention has been given to traditional Chinese medicine herbal ingredients that have been used to treat inflammatory diseases (Wang et al., J. Ethnopharmacol., 2013, 146:9-39). This attention is due to safety and efficacy of herbal medicine, lower risk of side effects, lower costs, and potential usage as adjunct treatments to Western medicine (Zhao et al., 2014, J. Tradit. Chin. Med., 34:145-9). Thus, providing the scientific basis for the active ingredients of herbal medicines further enhances the treatment of serious conditions and diseases associated with chronic inflammation.

Activated macrophages produce biologically active cytokines such as tumor-necrosis factor alpha (TNF-α) through intracellular signaling pathways through the nuclear factor kappa B (NF-κB) pathway (Yamamoto et al., Curr. Mol. Med., 2001, 1:287-96). This pathway involves numerous factors and kinases that are regulated by phosphorylation. Transcription factors that regulate the inflammatory response are sequestered in the cytoplasm by inhibitor molecules, such as inhibitor kappa B α (IκB α) (Mercurio et al., 1997, Science, 278:860-6; (Mercurio et al., 1997; Nywana et al., 2014). IκB α binding to the NF-κB transcription factor inhibits transactivation, translocation, and promoter binding (Ganchi, et al., 1992, Mol. Biol. Cell., 3:1339-52). When the necessary factors are recruited, the IκB α kinase (IKK) phosphorylates IκB α and releases NF-κB. NF-κB ultimately translocates into the nucleus to promote transcription of genes involved in inflammation, including the production and release of biologically active cytokines such as TNF-α and proinflammatory interleukins (IL). Released cytokines induce chemotaxis, vasodilation, and cell proliferation as well as differentiation. Current therapeutics using corticosteroids, monoclonal antibodies, and recombinant proteins suppress inflammation by preventing leukocyte activation or neutralizing TNF-α, which is the most potent cytokine released by various cell types to initiate amplification of inflammation (Aggarwal, 2003, Nature Rev. Immunol., 3:745-756).

In this study, we examined the anti-inflammatory effects of oligostilbenes, cis- and trans-gnetin H, isolated from the seeds of *Paeonia suffruticosa* on lipopolysaccharide (LPS)-stimulated human THP-1 cells (Chanput, et al., 2014, Int. Immunopharmacol., 23:37-45) with respect to the NF-κB pathway. We first examined the expression of proinflammatory cytokines (TNF-α, IL-1β, and IL-8). We then assessed the key inhibitory mechanism on signaling molecules in the NF-κB pathway by measuring the nuclear translocation of the activated NF-κB transcription factor, p65, and further examined the expression of activated/phosphorylated upstream kinase, IKK-β, and regulatory factor IκB α, associated with the NF-κB pathway.

Materials and Methods

Reagents.

THP-1 (ATCC, TIB-202) were purchased from American Type Culture Collection (Manassas, Va., USA). Lipopolysaccharide (LPS, *Salmonella enterica* serotype thyphimurium), dexamethasone, 3-(4-methylphenylsulfonyl)-2-propenenitrile (Bay 11-7082), staurosporine, dimethyl sulfoxide (DMSO), phorbol 12-myristate 13-acetate (PMA), and RPMI 1640 culture media were purchased from Sigma-Aldrich (St. Louis, Mo., USA). Fetal bovine serum (FBS), enhanced chemiluminescence luminol (ECL) substrate, penicillin/streptomycin, SDS-PAGE gels, and nitrocellulose membranes were obtained from Fisher Scientific (Pittsburgh, Pa., USA). Alamar blue was purchased from Life Technologies (Grand Island, N.Y., USA). ELISA kits and associated reagents were obtained from R&D Systems (Minneapolis, Minn., USA). Bovine serum albumin (BSA) was obtained from EMD Millipore (Billerica, Mass., USA). Cellomics NF-κB kit and BCA kit were purchased from Thermo Scientific (Waltham, Mass., USA). Antibodies for the Western blot analysis were purchased from Cell Signaling Technology (Danvers, Mass., USA).

Plant Material.

The seeds of *Paeonia suffruticosa* were collected in Tongling, Anhui Province, P.R. China, and a voucher specimen has been deposited in the Seed Resource Bank of the Institution of Medicinal Plant Development, Chinese Academy of Medical Science and Peking Union Medical College (Gao et al., 2015, J. Ethnopharmacol., 169:24-33).

Extraction and Isolation of Cis- and Trans-Gnetin H.

cis- and trans-gnetin H were extracted and isolated from the dried seeds of *Paeonia suffruticosa* as described previously (He et al., Chem. Pharm. Bull. 2010; 58:843-847). Briefly, the dried seeds were extracted with ethanol for 24 h at room temperature and then subfractionated using water, cyclohexane, chloroform, and ethyl acetate. cis- and trans-gnetin H were purified from the ethyl acetate extract and further fractionated using chloroform-methanol elution followed by ODS-A C18 reversed-phase silica gel (MeOH—H2O) and then purified by Sephadex LH-20 column chromatography. The compounds were suspended in DMSO to yield the desired concentration and stored at 4° C.

Maintenance and Differentiation of the THP-1 Cell Line.

THP-1 cells were maintained in RPMI 1640 medium supplemented with 10% complement-inactivated FBS and 1% penicillin/streptomycin (complete culture medium) at 37° C. with 5% $CO_2$ supplemented. Cell concentrations were adjusted to desired concentrations for each experiment by centrifugation at 500×g for 5 min and resuspended in complete culture medium with 100 nM of PMA. Cell concentration was adjusted to $5 \times 10^5$ cells/ml for all assays and $2.5 \times 10^5$ cells/ml were used for NF-κB nuclear translocation assay. Cells were seeded onto 96-, 24-, or 12-well plates and incubated for 48 to 72 h to allow for differentiation. Cells were washed with serum-free RPMI 1640 medium before each experiment to remove the undifferentiated cells.

Cell Viability Alamar Blue Assay.

Figure 9:
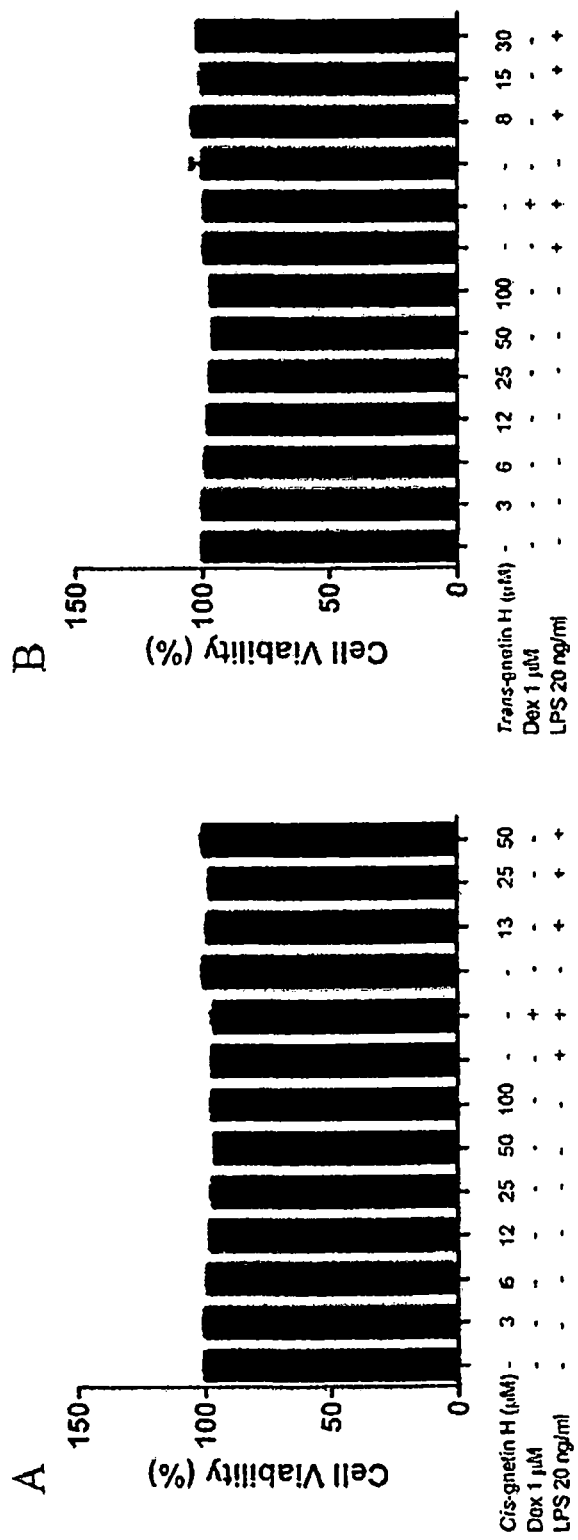
FIG. 9 shows the cytotoxic effect of cis- and trans-gnetin H on PMA-differentiated THP-1 macrophages. PMA-differentiated THP-1 cells were treated with various concentrations of cis- or trans-gnetin H and tested for relative viability using Alamar Blue assay. Cells were treated with cis-gnetin H at 3, 6, 13, 25, 50, 100 μM for 24 h and pretreated with 13, 25, 50 μM for 1 h with 20 ng/ml of LPS stimulation for 4 h to determine relative viability against untreated control (A). Cells were treated with trans-gnetin H at 3, 6, 13, 25, 50, 100 μM for 24 h and pretreated with 8, 15, 30 μM for 1 h with 20 ng/ml of LPS for 4 h to determine relative viability against untreated control (B). The viability assay was repeated in at least 3 independent experiments.

Differentiated THP-1 cells were treated with various concentrations of cis- and trans-gnetin H and 1 μM of dexamethasone for 24 h. Following treatment, the cell supernatants were replaced with culture medium containing 1× Alamar Blue reagent and incubated for an additional 20-24 h. Cell viability was assessed by measuring Relative Fluorescent Units (RFU) on the SpectraMax M2e microplate reader (Molecular Devices Inc., Sunnyvale, Calif., USA) at Ex 560 nm and Em 590 nm. The results were expressed as a percentage, relative to untreated control cells (FIG. 9). Untreated and LPS-treated cells were tested for the effect of DMSO as vehicle control.

Assessment of Cytokine Response by ELISA.

Differentiated THP-1 cells were pretreated with various concentrations of cis-gnetin H, trans-gnetin H, or 1 μM of dexamethasone for 1 h and stimulated with 20 ng/ml of LPS for 4 h. Dexamethasone is a synthetic glucocorticoid that suppresses cytokine response and was used as a positive control (Abraham et al., 2006, J. Exp. Med., 203:1883-9; Steer et al., J. Biol. Chem., 2000, 275(24):18432-40). Supernatants were collected for human cytokine ELISAs and the manufacturer's protocol was followed to assess the cytokine response. Cells remaining after the supernatant collection were tested for relative viability by Alamar Blue cytotoxicity assay as described earlier.

Indirect Immunofluorescence for NF-κB Nuclear Translocation.

Differentiated THP-1 cells were pretreated with 50 μM of cis-gnetin H, trans-gnetin H, or 10 μM of Bay 11-7082 for 1 h and stimulated with 1 μg/ml of LPS for 30 min. Bay 11-7082 is a compound that inhibits IKK α/β and IκB α phosphorylation and was used as a positive control (Juliana et al., 2010, J. Biol. Chem., 285:9792-802). Treated cells were fixed, permeabilized, blocked, and stained with NF-κB, p65 primary antibody, Dylight 488 conjugated secondary antibody, and Hoechst 33342 dye, sequentially. The Hoechst and DyLight fluorophores detect changes in nuclear morphology (blue fluorescence) and NF-κB distribution (green fluorescence) respectively. Nuclear Translocation Bioapplication software on the Arrayscan VTI reader was used for image acquisition and analysis. For each well, at least 400 cells were automatically acquired and analyzed. The translocation index was calculated by measuring the average intensity difference of NF-icB between the identified cytoplasmic region and nuclear region.

Western Blot Analysis.

Differentiated THP-1 cells were pretreated with various concentrations of cis-gnetin H, trans-gnetin H, or 10 μM of Bay 11-7082 for 1 h and stimulated with 1 μg/ml of LPS for 15 min. Cells were lysed with radio-immunoprecipitation assay (RIPA; 1% Triton X-100, 0.5% Sodium deoxycholate, 0.1% sodium dodecyl sulfate, 150 mM sodium chloride, and 50 mM Tris-chloride) lysis buffer that contained protease and phosphatase inhibitor cocktail. Cell lysates were then tested for protein concentration using a BCA protein assay, and diluted with RIPA lysis buffer to normalize protein concentration in all samples. Lysates were mixed with sample loading buffer containing bromophenol blue, glycerol, sodium dodecyl sulfate (SDS), and 2-mercaptoethanol (2ME). The separated proteins were then transferred onto nitrocellulose membrane and blocked with 5% BSA in 1× Tris-buffered saline (TBS) with 0.1% Tween-20 for 30 min. The blots were incubated with primary antibodies for p-65, phosphorylated p-65 (Ser536), IKK β, phosphorylated IKK α/β (Ser176/180), IκB α, and phosphorylated IκB α (Ser32) at 4° C. overnight or 1 h at 22° C. followed by incubation with HRP-conjugated secondary antibodies for 1 h at 22° C. The membranes were then developed by addition of ECL substrate and images were collected by ChemiDoc XRS+ system chemiluminescence imager (Bio-Rad, Hercules, Calif., USA).

Statistical Analysis.

All experiments were conducted at least three times independently. Western blot band intensity analysis was done by image lab software and statistical significance was performed by Graphpad Prism. Numeric values of treated groups were compared to control group and results were expressed as mean±SEM. Statistical significance was analyzed using one-way analysis of variance followed by Sidak test (Graphpad Prism). A value of *p<0.05 was set for significance.

Results

Cytotoxicity of Cis- and Trans-Gnetin-H on PMA-Differentiated THP-1 Macrophages.

We first examined the toxicity of cis- and trans-gnetin H in PMA-differentiated macrophages. Cells were pretreated with various concentrations of cis- and trans-gnetin H for 24 h and relative viability was accessed by Alamar Blue assay. The effect of compounds with LPS was also tested for relative viability. The viability test was done for every supernatant sample collection for cytokine response assay to show the suppression of cytokine response was not due to cell death. Neither cis- nor trans-gnetin H affected the viability of the cells at concentration 3, 6, 13, 25, 50, 100 μM after 24 h treatment (FIG. 9). The vehicle control, DMSO, was tested and showed no effect on viability of the cells (data not shown). Pretreatment with cis-gnetin H at 12.5, 25, 50 μM and LPS had no effect on cell viability (FIG. 9A). Pretreated with trans-gnetin H at 50 μM, however, showed decreased viability relative to the untreated control (FIG. 9B). Therefore, 7.5, 15, 30 μM of trans-gnetin H were used for the cytokine response assay.

The Effects of Cis- and Trans-Gnetin H on TNF-α, IL-1β, and IL-8 Response in LPS-Stimulated THP-1 Cells.

Figure 10:
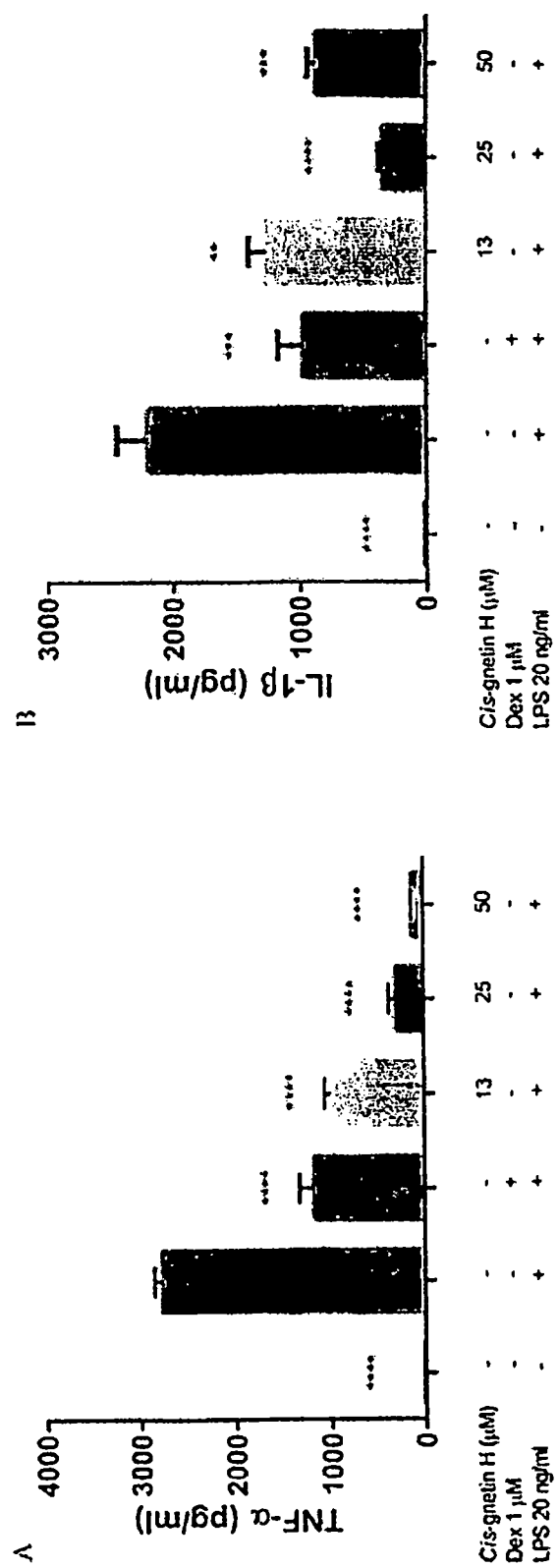
FIG. 10 shows cis- and trans-gnetin H inhibit TNF-α, IL-1β, and IL-8 responses in LPS-stimulated THP-1 cells. PMA-differentiated THP-1 cells were pretreated with 12.5, 25, and 50 μM of cis-gnetin H or 8, 15, 30 μM of trans-gnetin H for 1 h and stimulated with 20 ng/ml of LPS for 4 h. The concentration of TNF-α (A and D), IL-1β (B and E), and IL-8 (C and F) in supernatants was determined by ELISA. Results are presented as the mean±SEM for triplicate measurements of at least 3 independent experiments. *p<0.05, p<0.01, *p<0.001, ****p<0.0001 compared with LPS-treated group.
Figure 10:
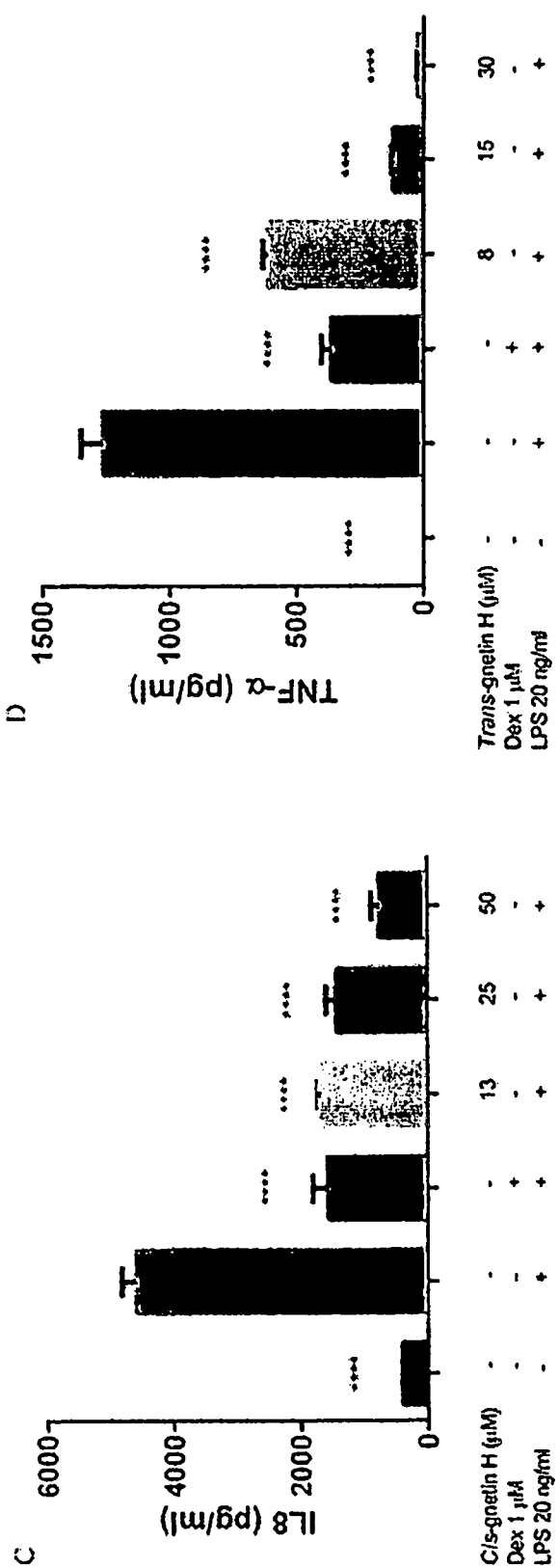
Figure 10:
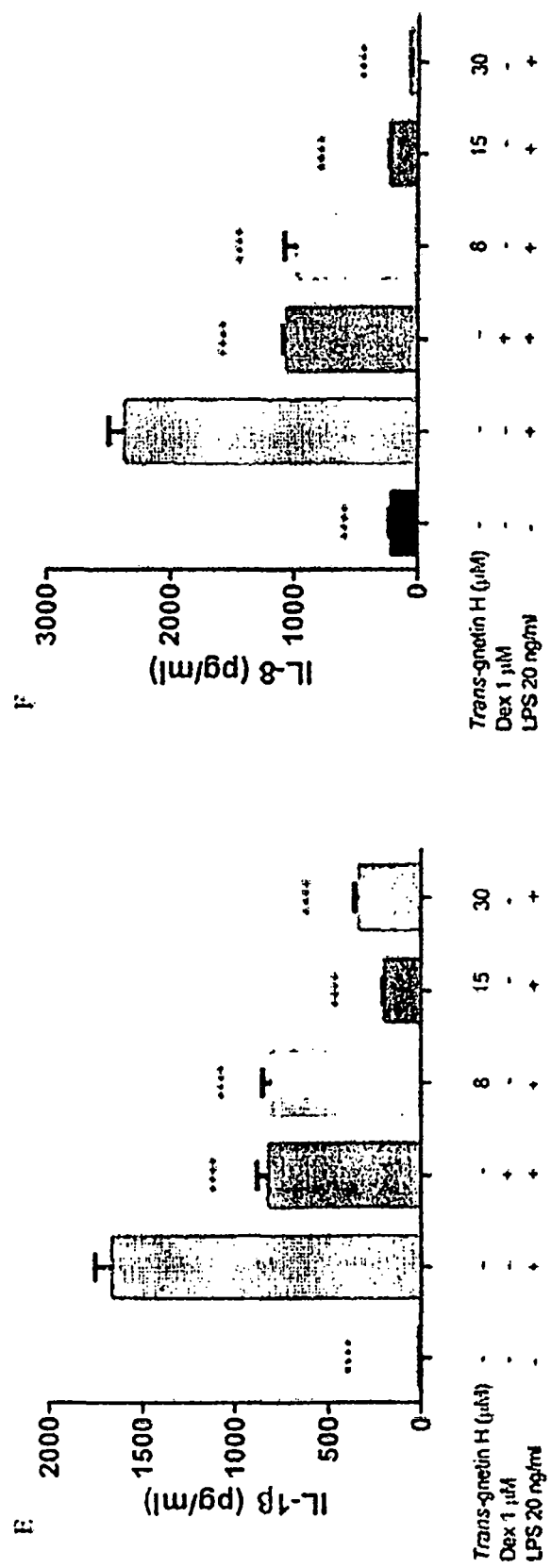
Figure 11:
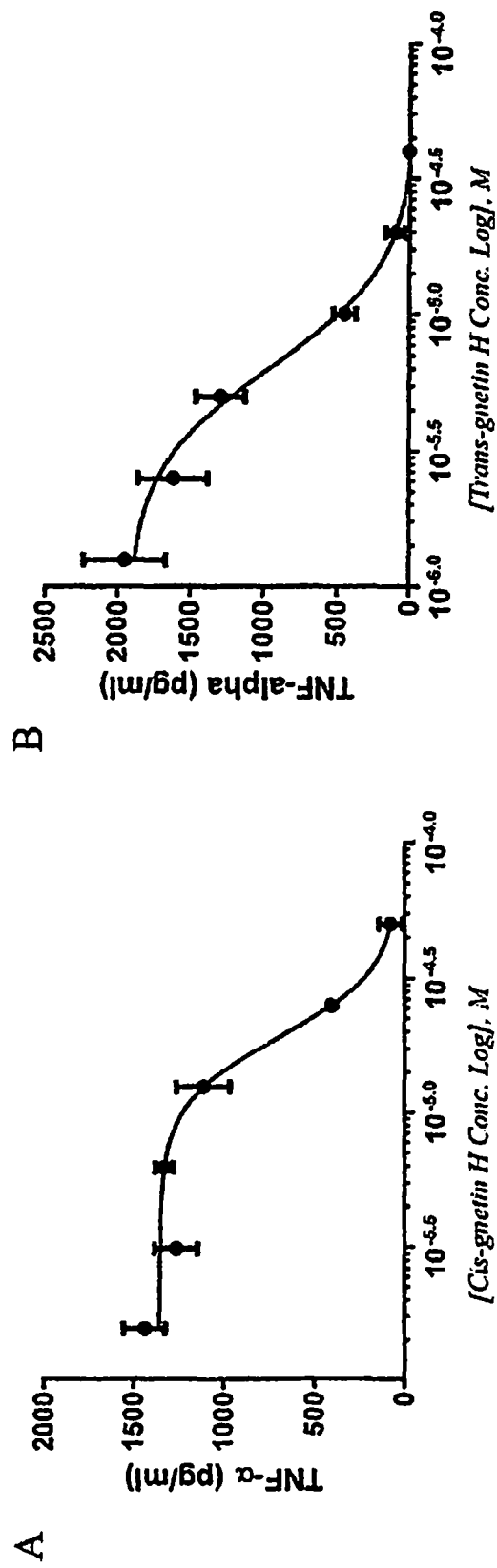
FIG. 11 shows the TNF-α $IC_{50}$ curves of cis- and trans-gnetin H. PMA-differentiated THP-1 cells were pretreated with various concentrations of cis-(A) or trans (B)-gnetin H for 1 h and stimulated with LPS for 4 h. Supernatants were tested for human TNF-α ELISA. The $IC_{50}$ curves were obtained using Graphpad Prism. $IC_{50}$ value of cis-gnetin H was 19 μM and $IC_{50}$ value of trans-gnetin H was 6 μM.

We then investigated the effects of cis- and trans-gnetin H on expression of the inflammatory cytokines, TNF-α, IL-1p, and IL-8 in LPS-induced THP-1 macrophages. As FIG. 10 shows, LPS at 20 ng/ml concentration increased the expression of TNF-α, IL-1β, as well as IL-8. DMSO did not affect cytokine response in LPS-treated THP-1 cells (data not shown). Dexamethasone (positive control) at 1 μM showed 58%, 56%, and 63% inhibition of TNF-α, IL-1β, and IL-8 respectively. Cells treated with cis- and trans-gnetin H showed significant inhibition of TNF-α, IL-1β, and IL-8 (p<0.05). We then measured the concentrations of cis- and trans-gnetin H that inhibited 50% of TNF-α ($IC_{50}$) and calculated that $IC_{50}$ values were 19 μM for cis-gnetin H and 6 μM for trans-gnetin H (FIG. 11).

The Effects of Cis- and Trans-Gnetin H on NF-κB Transcription Factor Nuclear Translocation.

Figure 12:
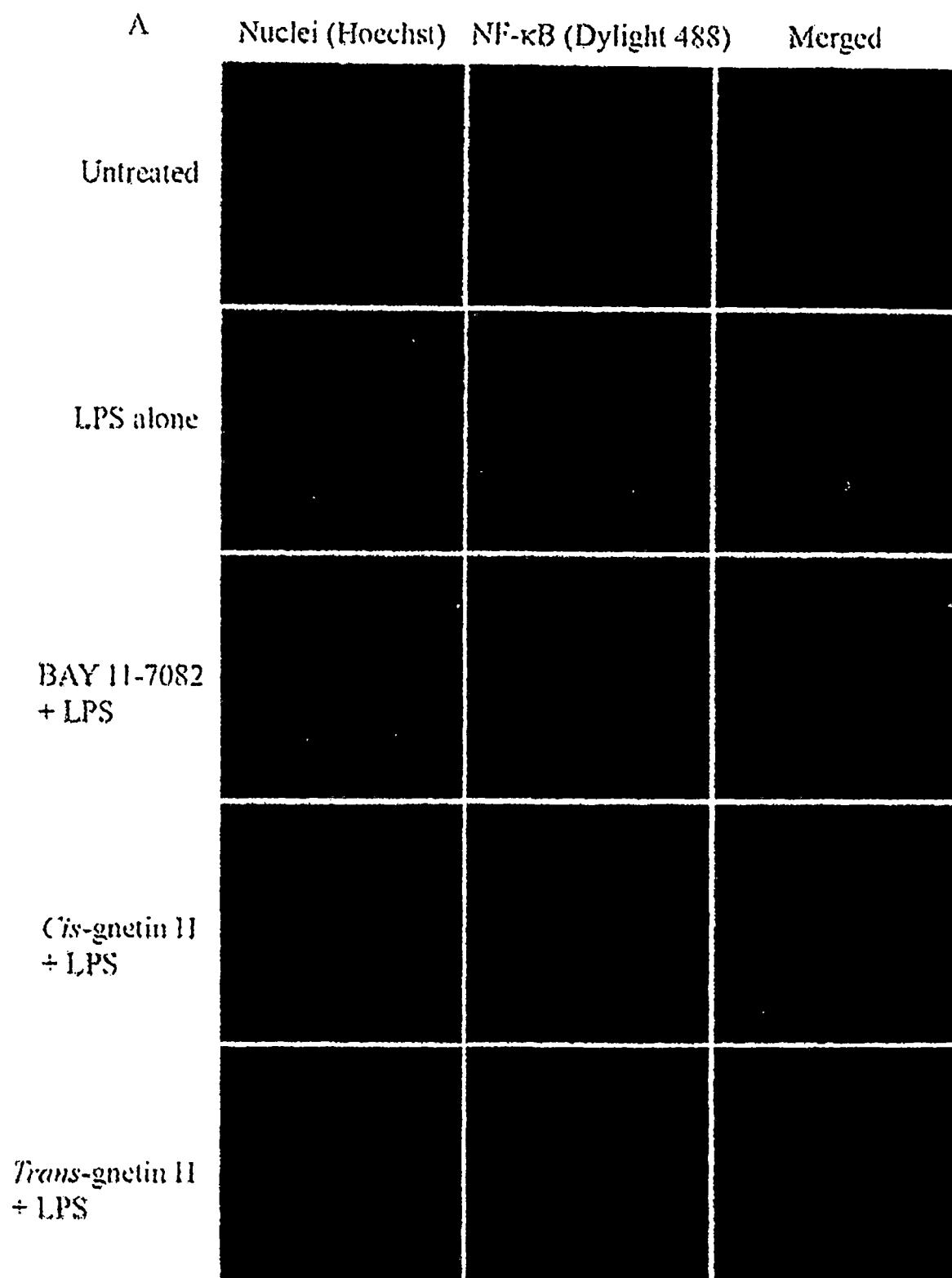
FIG. 12 shows the effects of cis- and trans-gnetin H on NF-κB transcription factor nuclear translocation. PMA-differentiated cells were treated with cis-gnetin H at 50 μM, trans-gnetin H at 30 μM, or Bay 11-7082 at 10 μM for 1 h and stimulated with 100 ng/ml LPS for 30 min. The transcription factor p65 was stained with rabbit anti-p65 followed by Dylight 488-conjugated secondary antibody (green fluorescence) and Hoechst 33342 dye (blue fluorescence), sequentially (A). The numeric index of nuclear fluorescence of p65 was collected using Nuclear Translocation Bioapplication software on the Arrayscan VTI reader (B).
Figure 12:
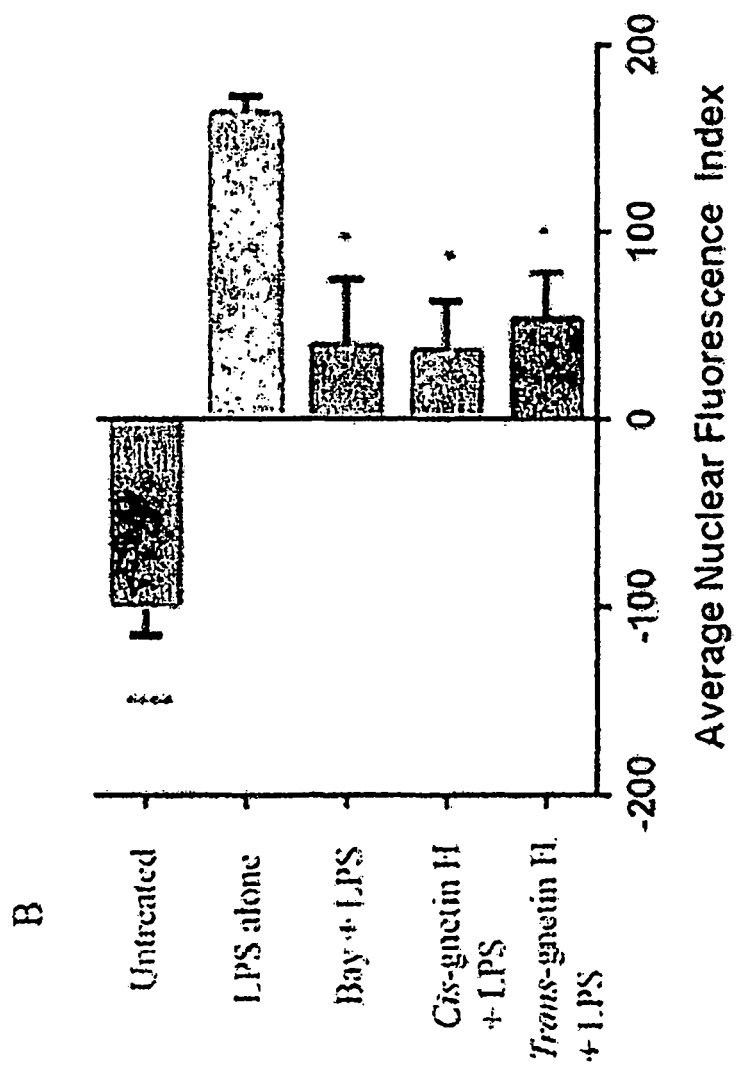

We next examined the effects of cis- and trans-gnetin H on NF-κB nuclear translocation by targeting p65 (RelA), a significant transcription factor in NF-κB pathway. As FIG. 12A shows, p65 (green fluorescence) remained in the cytoplasm in untreated cells whereas p65 translocated into the nucleus in LPS-challenged cells. Bay 11-7082 inhibited the p65 nuclear translocation and both cis- and trans-gnetin H inhibited the p65 nuclear translocation as shown in FIG. 12.

The Effects of cis- and trans-Gnetin H on IKKβ, IκB α, and p65 in NF-κB Pathway.

Figure 13:
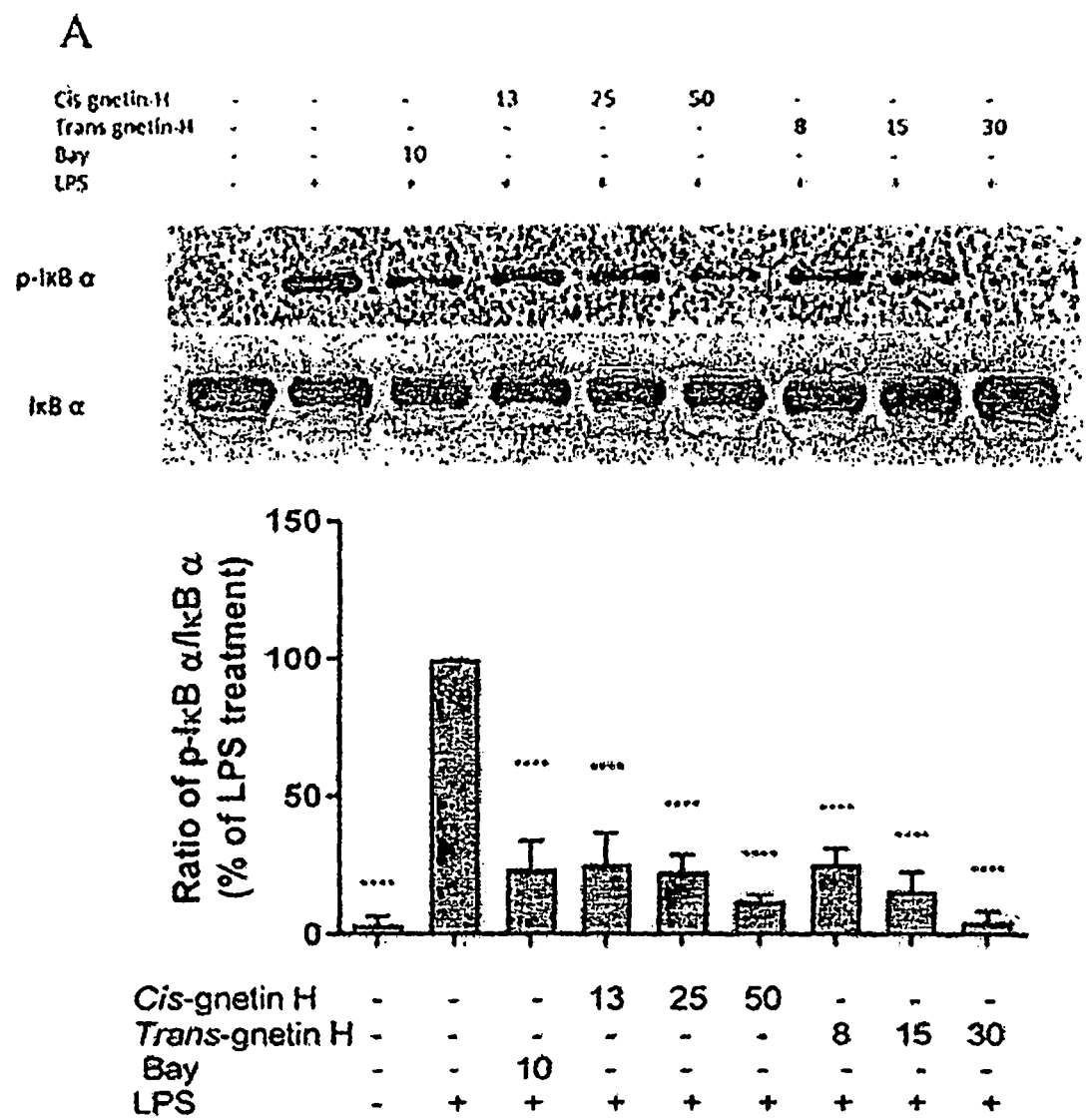
FIG. 13 shows the effects of cis- and trans-gnetin H on IKK β, IκB α, and p65 in NF-κB pathway. PMA-differentiated cells were pretreated with 12.5, 25, and 50 μM of cis-gnetin H or 7.5, 15, and 30 μM of trans-gnetin H for 1 h and stimulated with 1 μg/ml of LPS for 15 min. Phosphorylated IκB α (Ser32) and total IκB α (A), and phosphorylated p65 (Ser536) and total p65 (B), phosphorylated (Ser176/180) IKK-β and total IKK-α β (C) were measured by Western blotting. Data are represented as the mean±SEM for at least three independent experiments. *p<0.05, p<0.01, *p<0.001, ****p<0.0001 compared with LPS-treated group.
Figure 13:
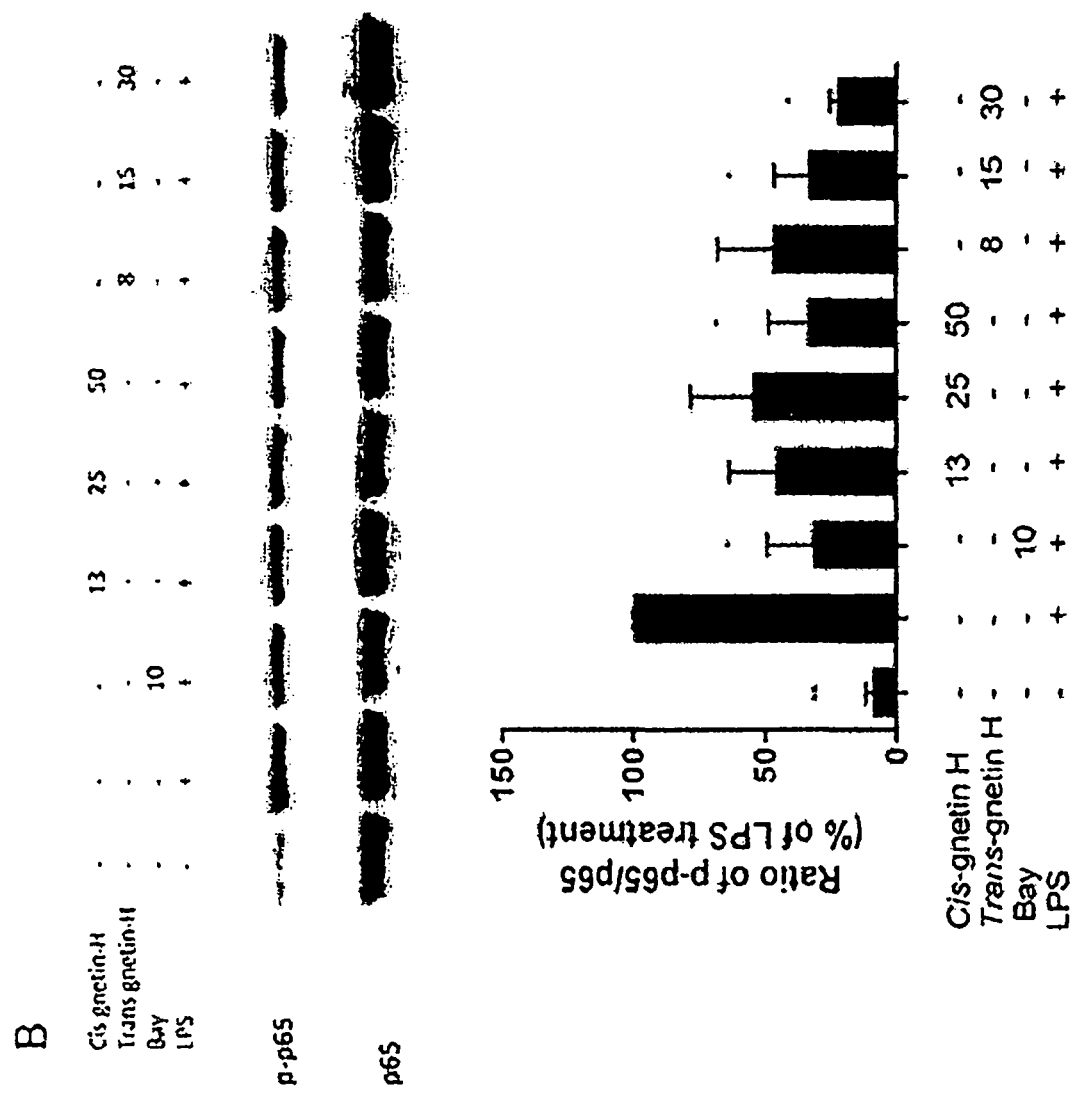
Figure 13:
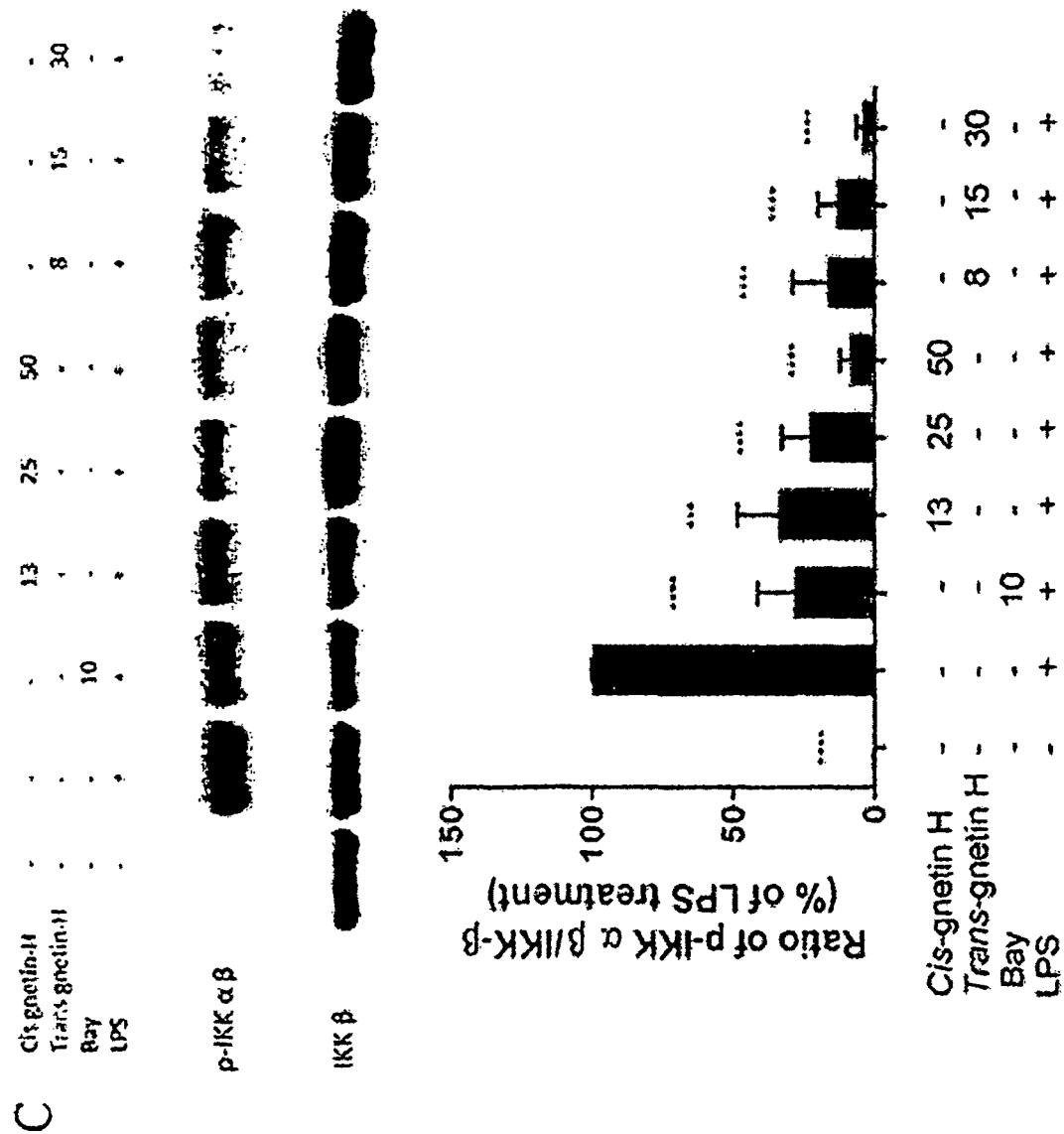
Figure 14:
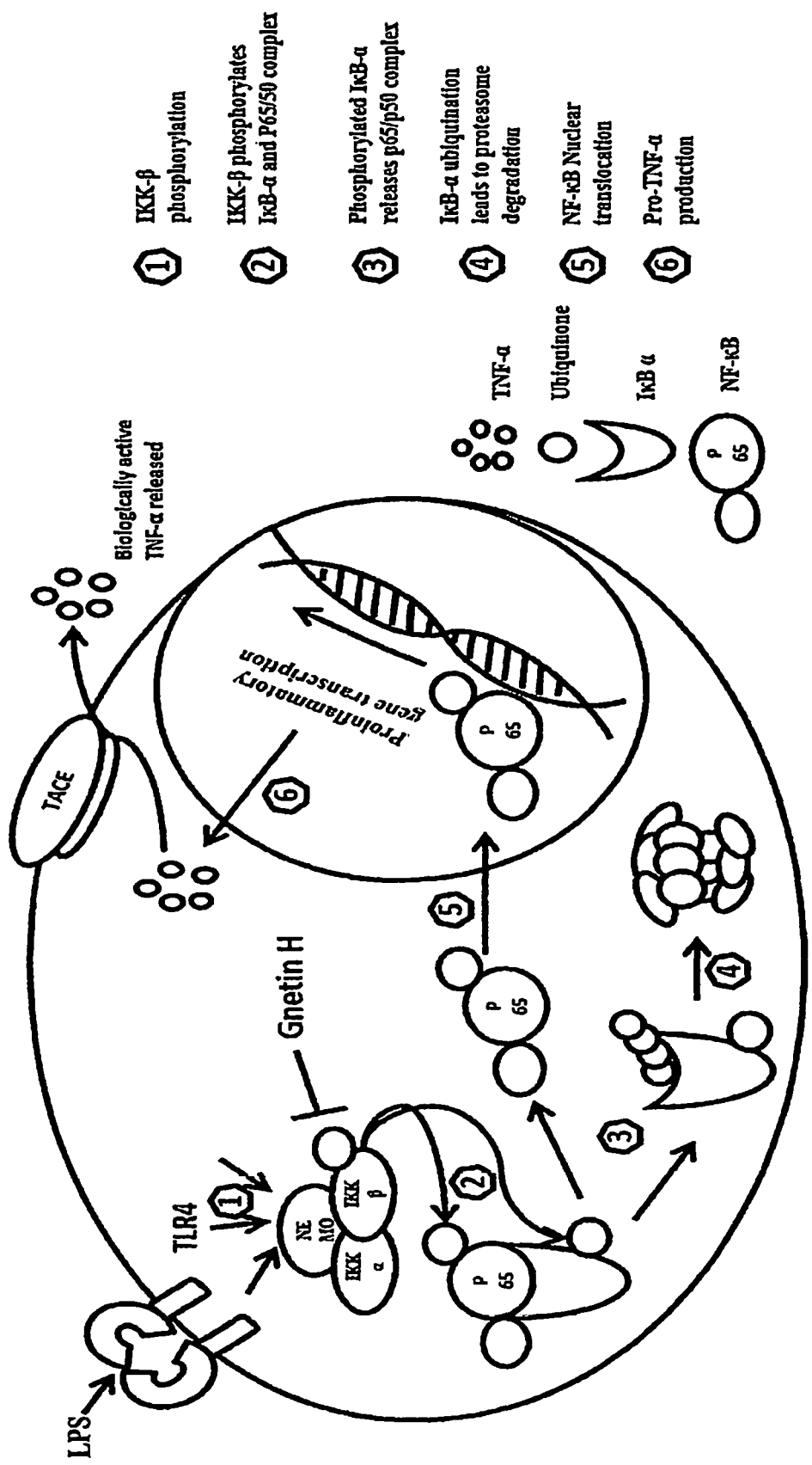
FIG. 14 shows a schematic of the NF-κB pathway, its role in inflammation, and a potential mechanism underlying the anti-inflammatory effect of cis- and trans-gnetin H.

We also measured LPS-induced activation of important mediators in the NF-κB pathway: IKK β, IκB α, and p65. Our results showed that in LPS-stimulated cells IκB α phosphorylation was also significantly inhibited by cis- and trans-gnetin H in a concentration-dependent manner (FIG. 13A). p65 phosphorylation was only significantly inhibited at the highest concentration, 50 μM, of cis-gnetin H treated cells but both 15 and 30 μM concentrations of trans-gnetin H significantly inhibited p65 phosphorylation in a concentration-dependent manner. IKK 13 phosphorylation was also significantly inhibited by cis- and trans-gnetin H (FIG. 13C).

Discussion

Inflammation is an important component of immune responses that are associated with multiple human diseases. Many of these diseases currently do not have effective treatments to control the inflammatory response. Currently available preventive therapies for chronic inflammatory and autoimmune diseases block the cytokine response, particularly TNF-α. Anti-TNF therapy has been clinically demonstrated as the most effective approach to control inflammation (Postal et al., Cytokine, 2011, 56:537-43). Cytokines such as TNF-α that are released by various cell types including macrophages and lymphocytes play a critical role in inflammatory processes by inducing chemotaxis, activation of various types of cells, and amplification of inflammation (Thalayasingam et al., Best Pract. Res. Clin. Rheumatol., 2011, 25:549-67; Yamamoto et al., Curr. Mol. Med., 2001, 1:287-96). Studies have shown that suppressing the inflammation process reduces the painful symptoms and increases the quality of life in patients that suffer from severe conditions involved in chronic inflammatory diseases (Impellizzeri et al., Pharmacol. Res., 2014, 81:91-102; Postal et al., Cytokine, 2011, 56:537-43). The present study clearly demonstrates that cis- and trans-gnetin H effectively suppress LPS-induced cytokines, TNF-α, IL-1β, and IL-8, in supernatants of cell culture in a concentration-dependent manner without affecting the viability of the cells. Interestingly, trans-gnetin H showed more effective suppression in all cytokines tested than cis-gnetin H and fold changes dramatically increases in trans-gnetin H treated cells at 30 μM (FIG. 10). These results suggest that there is differential effect of cis- and trans-gnetin H, likely as a result of the differences in the olefinic moiety.

LPS-activated macrophages produce biologically active cytokines such as TNF-α through intracellular signaling pathways, such as the NF-κB pathway (Medvedev et al., 2002, J. Immunol., 169:5209-16; Yamamoto et al., Curr. Mol. Med., 2001, 1:287-96). p65, also known as RelA, is one of the 5 members of NF-κB transcription factors that are most abundant and most responsible for NF-κB pathway (Sasaki et al., J. Biol. Chem., 2005, 280:34538-47; Schmitz et al., EMBO J., 1991, 10:3805-17; Yang et al., J. Immunol., 2003, 170:5630-5). When the NF-κB pathway is activated, phosphorylated p65 translocates into the nucleus and promotes the transcription of various genes including genes encoding cytokines. In this study, we demonstrated that cis- and trans-gnetin H effectively block the translocation of p65 into the nucleus. We also further explored biological mechanism of the cis- and trans-gnetin H in suppressing the cytokine response that lies upstream of the NF-κB nuclear translocation.

The NF-κB pathway involves numerous factors and kinases that are regulated mainly through recruitments and phosphorylation processes. LPS binds to CD14 and dimerizes TLR4, triggering recruitment of a series of intracellular proteins including MYD88, TIR, RIF, TRAM, and the TRAF family (Laird et al., 2009, J. Leukoc. Biol., 85:966-77) and subsequently activates several kinases including IRAK1, MEKK1 (Lee et al., 1998, Proc. Nat'l. Acad. Sci. USA, 95:9319-9324), MEKK3 (Qin et al., J. Biol. Chem., 2006, 281:21013-21), IRAK1 (Yao et al., J. Biol. Chem., 2007, 282:6075-89), IKKε/TBK1 (Smith et al., Biochem. J., 2011, 434:537-48) and TAK1 (Sakurai, Trends Pharmacol. Sci., 2012, 33:522-30; Shim et al., Genes Dev., 2005, 19:2668-81) that phosphorylate IKK-β (Israel, 2010, Cold Spring Harb. Perspect. Biol., 2:a000158; Laird et al., J. Leukoc. Biol., 2009, 85:966-77). The exact mechanism of LPS-induced IKK-β phosphorylation is obscure, however, IKK-β activation is required to activate NF-κB pathway in LPS-induced macrophages (Israel, Cold Spring Harb. Perspect. Biol., 2010, 2: a000158). As our results show, cis- and trans-gnetin H significantly inhibit the phosphorylation of IKK-β in a concentration-dependent manner (FIG. 13C). Activation of IKK-β leads to release and proteasome-dependent degradation of IκB α. IκB α binding to p65 inhibits transactivation, translocation, and promoter binding. Upon phosphorylation of IκB α, p65/50 complex is released and ultimately translocates into the nucleus. Our results suggest cis- and trans-gnetin H significantly abrogate the phosphorylation of IκB α (FIG. 13A), as indicated by a decrease in IKK-β activation.

Interestingly, we observed a higher level of phosphorylation of p65 than expected (FIG. 13B). This observation suggests that there are other kinases involved in the regulation of p65. IKK-β is not the mechanism phosphorylate IκB α, but also phosphorylates p65 at serine residue 536 which is a hallmark of p65 activation. The phosphorylation of p65 remains controversial in that there are multiple kinases that regulate the activation of p65 including IκB α-independent phosphorylation. Recently, Buss et al. identified that cyclin-dependent kinase 6 also phosphorylates p65 at serine 536 residue (PLoS One, 2012, 7:e51847). Moreno et al. suggested serine 536 phosphorylated p65 predominantly remained in the cytosol while serine 468 phosphorylated p65 by IKKε/TBK1 mainly localized in the nucleus (Nucl. Acids Res., 2010, 38:6029-44). This finding suggests that phosphorylation of p65 at serine 536 does not correlate with nuclear translocation and that cis- and trans-gnetin H may exert inhibition of IKKε/TBK1 activity as well as IKK-β.

Macrophages are key immune cells that regulate inflammation process and therefore, suppressing macrophages activation can alleviate the progression of chronic inflammation and slow the severity of disease progression caused by chronic inflammation. Our results suggest that cis- and trans-gnetin H compounds can significantly limit the cytokine response in human THP-1 macrophages with different potencies. Experiments are in progress to better understand the mechanism or target for these compounds, however, our results in support that the inhibition of IKK-β activation which is an important kinase for NF-κB pathway. In conclusion, we suggest cis- and trans-gnetin H have potential pharmacological usages for diseases and conditions characterized by chronic inflammation.

The complete disclosures of all patents, patent applications including provisional patent applications, publications including patent publications and nonpatent publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for treating cancer in a subject, the method comprising:
   administering to the subject a composition comprising an effective amount of cis-gnetin H, wherein the cis-gnetin H is substantially free of trans-gnetin H,
   wherein the cancer is selected from bone cancer, breast cancer, and lung cancer.

2. The method of claim 1, wherein the cancer is a metastatic cancer.

3. The method of claim 1, comprising administering the composition in an amount effective to inhibit or reverse the growth of a tumor in the subject.

4. The method of claim 3, wherein the tumor is a solid tumor.

5. The method of claim 3, wherein the tumor is a fast growing tumor.

6. The method of claim 1, wherein the subject is a domestic animal, a domesticated animal, a zoo animal, or a human.

7. The method of claim 1, wherein the composition comprises an extract prepared from *Paeonia suffruticosa* seeds.

8. The method of claim 1, wherein the composition further comprises a pharmaceutically acceptable carrier.

9. The method of claim 1, wherein the composition further comprises an additional active agent selected from the group consisting of an anticancer agent, antiangiogenic agent, a chemopreventive agent, an anti-inflammatory agent, a cytokine, a chemokine, a therapeutic antibody, an immunogen, an antigen, an adjuvant, or an antioxidant, an immunomodulatory compound, a biologic compound, an antineoplastic agent, and a chemotherapeutic agent.

10. The method of claim 9, wherein the additional active agent is a non-naturally occurring compound.

* * * * *